US012083092B2

(12) United States Patent
Neyts et al.

(10) Patent No.: US 12,083,092 B2
(45) Date of Patent: Sep. 10, 2024

(54) ANTIVIRAL 1,3-DI-OXO-INDENE COMPOUNDS

(71) Applicants: Novartis AG, Basel (CH); Katholieke Universiteit Leuven, Leuven (BE); Korea Research Institute of Chemical Technology, Daejeon (KR)

(72) Inventors: Johan Neyts, Kessel-Lo (BE); Daniel Poon, Piedmont, CA (US); Keith Bruce Pfister, Emeryville, CA (US); Young-Sik Jung, Daejeon (KR); Soo Bong Han, Daejeon (KR); Yashwardhan R. Malpani, Daejeon (KR); Prashant Chakrasali, Daejeon (KR); Sang-Ho Lee, Daejeon (KR); Chong-Kyo Lee, Daejeon (KR); Chonsaeng Kim, Daejeon (KR); Jin Soo Shin, Daejeon (KR); Hae Soo Kim, Daejeon (KR)

(73) Assignees: Novartis AG, Basel (CH); Katholieke Universiteit Leuven, Leuven (BE); Korea Research Institute of Chemical Technology, Daejeon (KR)

( * ) Notice: Subject to any disclaimer, the term of this patent is extended or adjusted under 35 U.S.C. 154(b) by 707 days.

(21) Appl. No.: 17/235,140

(22) Filed: Apr. 20, 2021

(65) Prior Publication Data

US 2021/0322362 A1 Oct. 21, 2021

Related U.S. Application Data

(60) Provisional application No. 63/012,770, filed on Apr. 20, 2020.

(51) Int. Cl.
*A61K 31/343* (2006.01)
*A61P 31/14* (2006.01)
*C07D 307/93* (2006.01)

(52) U.S. Cl.
CPC ............ *A61K 31/343* (2013.01); *A61P 31/14* (2018.01); *C07D 307/93* (2013.01)

(58) Field of Classification Search
None
See application file for complete search history.

(56) References Cited

U.S. PATENT DOCUMENTS

| | | | |
|---|---|---|---|
| 3,892,807 | A | 7/1975 | Sahm |
| 3,984,552 | A | 10/1976 | Cragoe et al. |
| 4,569,945 | A | 2/1986 | Campbell et al. |
| 9,346,749 | B2 | 5/2016 | Jung et al. |
| 9,464,067 | B2 | 10/2016 | Jung et al. |
| 9,790,197 | B2 | 10/2017 | Jung et al. |
| 9,833,423 | B2 | 12/2017 | Jung et al. |
| 9,890,133 | B2 | 2/2018 | Jung et al. |
| 9,951,058 | B2 | 4/2018 | Jung et al. |
| 2002/0091261 | A1 | 7/2002 | Bold et al. |
| 2010/0133117 | A1 | 6/2010 | Gao |
| 2010/0261706 | A1 | 10/2010 | Jagtap et al. |
| 2014/0114068 | A1 | 4/2014 | Jung et al. |
| 2021/0323947 | A1 | 10/2021 | Neyts et al. |

FOREIGN PATENT DOCUMENTS

| | | | | |
|---|---|---|---|---|
| CA | 2838703 | A1 * | 12/2012 | ........... A61K 31/343 |
| CN | 103764140 | B | 5/2017 | |
| EP | 0481708 | A1 | 4/1992 | |
| EP | 409410 | B1 | 3/1996 | |
| EP | 1081138 | B1 | 9/2004 | |
| EP | 2324820 | B1 | 3/2016 | |
| EP | 2722042 | B1 | 5/2019 | |
| FR | 2392951 | A2 | 12/1978 | |
| GB | 1425295 | A | 2/1976 | |
| GB | 1533388 | A | 11/1978 | |
| JP | 60109541 | A | 6/1985 | |
| JP | 2001089455 | A | 4/2001 | |
| JP | 2014523417 | A | 9/2014 | |
| JP | 2016504321 | A | 2/2016 | |
| RU | 2207132 | C2 | 6/2003 | |
| SU | 725559 | A1 | 3/1980 | |
| UA | 79834 | C2 | 7/2007 | |

(Continued)

OTHER PUBLICATIONS

Oberste. Viral Infections of Humans, 2014, pp. 225-252 (Year: 2014).*

Aleman, J. et al., "Organocatalytic Highly Enantioselective ά-Arylation of ß-Ketoesters", Angewandte Chemie International Edition, 2007, vol. 46, pp. 5515-5519.

Almog, Joseph et al., "The reaction between phloroglucinol and vic polycarbonyl compounds: extension and mechanistic elucidation of Kim's synthesis for bipolarofacial bowl-shaped compounds", Tetrahedron 65, (2009), pp. 7954-7962.

Arens, A., et al., "2-Amino derivatives of 4,5-and 5,6-dimethoxy-2-phenylindan-1,3-diones," Latvijas PSR Zinatnu Akademijas Vestis, Kimijas, 1966, vol. 3, pp. 342-346.

Arens, A., et al., "Amino derivatives of 2-piperonyl-1,3-idandione," Zhurnal Obshchei Khimii, 1964, vol. 34, No. 2, pp. 442-445.

(Continued)

*Primary Examiner* — Noble E Jarrell

(74) *Attorney, Agent, or Firm* — Sheppard Mullin Richter & Hampton LLP

(57) ABSTRACT

This disclosure provides compounds of Formula (I)

[I]

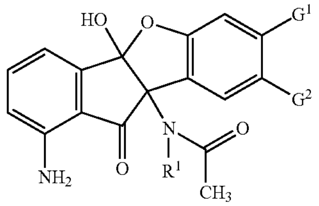

as described herein, along with pharmaceutically acceptable salts, pharmaceutical compositions containing such compounds, and methods to use these compounds, salts and compositions for treating viral infections.

31 Claims, No Drawings

(56) References Cited

FOREIGN PATENT DOCUMENTS

| | | | |
|---|---|---|---|
| WO | 2003082265 | A2 | 10/2003 |
| WO | 2004041201 | A2 | 5/2004 |
| WO | 2004041812 | A1 | 5/2004 |
| WO | 2004087153 | A2 | 10/2004 |
| WO | 2010003023 | A2 | 1/2010 |

OTHER PUBLICATIONS

Arens, A., et al., "Isomerization of 2-amino-2-substituted 1,3-indandiones," Latvijas PSR Zinatnu Akademijas Vestis, Kimijas Serija, 1980, vol. 6, pp. 677-691.

Arens, Augusts, et al., "2-Amino-2-halophenyl-1,3-indandiones," Latvijas PSR Zinatnu Akademijas Vestis, Kimijas Serija, 1969, vol. 4, pp. 446-451.

Arens, Augusts, et al., "Reduction of aminodicarboxylic compounds. III. 2-Alkylamino-2-phenyl-3-indanon-1-ol and 2-alkylamino-2-phenyl-1,3-indandiol," Journal of Organic Chemistry of the USSR, 1969, vol. 5, No. 9, pp. 2094-2097.

Benders, J. et al., "Esr spectra of semidiones derived from indandione-1,3," Journal of Molecular Structure, vol. 19, (Dec. 1, 1973), pp. 431-440.

Bite, Dz., et al., "Substituted thiourea B-dicarbonyl compounds. IX. Spectroscopic study of 2-substituted N-[1, 3-indandion-2-yl] thiourea and 2-(2-iminothiazolidin-3-yl]-2-substituted 1, 3-indandiounes," Latvijas PSR Zinatnu Akademijas Vestis Kimijas Serija, 1969, vol. 1, pp. 109-112.

Black, D.S.C., et al., "Reactions of Ninhydrin with Activated Anilines: Formation of Indole Derivatives", Tetrahedron, (1994), vol. 50, No. 37, pp. 10983-10994.

Briede, V., et al., "4,5-Dimethoxy-2-B-naphthyl-1,3-indandione," Latvijas PSR Zinatnu Akademijas Vestis, Kimijas Serija, 1967, vol. 3, pp. 329-333.

Bullington, J.L. et al., "Synthesis of Spiro[2H-indole]-3,3'-diones and Spiro[benzofuran-2,1'-isobenzofuran]-3,3'-diones via Transannular Reactions of Eight Membered Ring Intermediates", Journal of Heterocyclic Chemistry, vol. 35 (Mar.-Apr. 1998), pp. 397-403.

Bullington, James L., et al., "Synthesis of tetrahydroineno[1,2-b] indol-10-ones and Their rearrangement to [2] Benzopyrano[4,3-b]indol-5-ones", Journal of Organic Chemistry, vol. 58, No. 18, (1993), pp. 4833-4836.

Butera, John A., "Synthesis and Potassium Channel Opening Activity of Substituted 10H-Benzo[4,5]furo[3,2-b] indole- and 5, 10-Dihydroindeno[1,2-b] indole-1-carboxylic Acids", Bioorganic & Medicinal Chemistry Letters, 2001, vol. 11, pp. 2093-2094.

Courant, J. et al., "1,3-Indandiones VIII. 2-Hydroxy-2-indolyl-1, 3-indandiones, 2-(indol-3-ylmethylene indandione and derivatives: search for anti-inflammatory activity," European Journal of Medicinal Chemistry, Editions Scientifique Elsevier, Paris, FR., vol. 24, No. 2, (Mar. 1, 1989), pp. 145-154.

Das, S. et al., "A Facile Synthesis of Benzofuroisocoumarins from C-2 Arylated 1,3-Indanediones", Synlett, 2006, vol. 2, pp. 207-210.

Das, Suven et al., "A simple synthesis of 4-substituted 2,3-benzoxazinones from C-2 arylated 1,3-indanediones", Tetrahedron Letters, vol. 52, No. 25, (Apr. 27, 2011) pp. 3243-3246.

Diana, Guy D. "Inhibitors of Picornavirus Replication", Current Medicinal Chemistry-Anti-Infective Agents, vol. 2. No. 1. (Mar. 2003), pp. 1-12.

Eckstein, Zygmunt, et al., "Infrared absorption spectra of 2-nitroindandione derivatives," Bulletin de l'Academie Polonaise des Sciences, Serie des Sciences Chimiques, 1960, vol. 8, No. 10, pp. 579-586.

Extended European Search Report for EP 12799827.6, mailed Nov. 19, 2014.

Extended European Search Report for EP 12800577.4, mailed Mar. 24, 2015.

Grinsteins, V., et al., "Synthesis and study of thioureas. Infrared spectra of 2-ary1-2-thiocarbamido-1,3-indandiones," Latvijas PSR Zinatnu Akademijas Vestis, Kimijas Serija, 1972, vol. 4, pp. 441-444.

Groarke, James M. et al. "Attenuated Virulence of Pleconaril-Resistant Coxsackievirus B3 Variants", The Journal of Infectious Diseases, (Jun. 1999), vol. 179(6); pp. 1538-1541.

Gudriniece, E., et al., "2-Azido-2-substituted indan-1,3-dione," Doklady Akademii Nauk SSSR, 1966, vol. 171, No. 4, pp. 869-871.

Hark, Richard R. et al. "Synthetic studies of novel ninhydrin analogs", Can. J. Chem., vol. 79, (2001); pp. 1632-1654.

Hashimoto, Suzumi et al., "Dynamic behavior of cyclic hemiacetals of 2-Hydroxy-2-(2-hydroxyphenyl)-1,3-Indandione derivatives", Chemistry Letters, vol. 37, No. 7, (2008), pp. 696-697.

Heffner, Robert J., et al., "A Synthesis of Two Novel Benzo[f]Ninhydrin Analogs: 6-Methoxybenzo[f]Ninhydrin and Thieno[f]Ninhydrin", Synthietic Communications, 21(8&9), (1991), pp. 1055-1069.

Hieffner, Robert J., et al., "Synthetic Routes To Ninhydrines, Preparation of Ninhydrin, 5-Methoxyninhydrin, and 5-(Methylthio)Ninhydrin," Synthetic Communications, 21(21), (1991), pp. 2231-2256.

Heinz, Beverly A. et al., "The Antiviral Compound Enviroxime Targets the 3A Coding Region of Rhinovirus and Poliovirus", Journal of Virology, vol. 6, No. 7, (Jul. 1995), pp. 4189-4197.

International Search Report and Written Opinion of the International Searching Authority for PCT/KR2012/004804, mailed Dec. 28, 2012.

International Search Report and Written Opinion of the International Searching Authority for PCT/KR2012/004806, mailed Dec. 6, 2012.

International Search Report for Application No. PCT/KR2013/011668, dated Mar. 31, 2014.

International Search Report, issued in PCT/EP2021/060263, dated Jun. 4, 2021.

International Search Report, issued in PCT/EP2021/060271, dated Jul. 23, 2021.

Jasinskas, L., et al., "Synthesis of secondary amines of 4-methyl-2-phenylindandione," Lietuvos TSR Aukstuju Mokyklu Mokslo Darbai, Chem. Ir Chem. Technol., 1965, vol. 7, pp. 77-80.

Jeyachandran, Malaichamy et al., "Synthesis, Antimicrobial, and Anticoagulant Activities of 2-(Arylsulfonyl) indane-1,3-diones", Organic Chemistry International, vol. 2, No. 4, (Jan. 1, 2011), pp. 175-179.

Kapoor, Mona et al., "Stereoselective Synthesis of Z-3-alkoxy-2-[(4'-methoxyphenyl)methylidene]-1(3H)-isobenzofuranones", Tetrahedron Letters, vol. 59, No. 27, pp. 5027-5031, (Jun. 30, 2003).

King, Med. Chem: Principle and Practice (1994), pp. 206-208.

Kundu, Sandip Kumar et al., "6-(alpha-Hydroxy-alpha-aryl/naphthyl)methyl-3,4-dihydro-2,5-benzodiazocin-1(2H)-ones and diphenylmethanes from C-2 arylated 1,3-indanediones", Journal of Chemical Research, vol. 11, (2004), pp. 781-783.

Kundu, Sandip Kumar et al., "Theoretical studies of the acid-catalyzed condensation of ninhydrin with aromatic compounds", Indian Journal of Chemistry, Section B: Organic Chemistry, vol. 43B, No. 10, (2004), pp. 2212-2216.

Kuprava et al., Soobshcheniya Akademii Nauk Gruzinskoi SSR (1964), Vo. 36(3), pp. 573-577.

Ledford, Rebecca M. et al., "VP1 Sequencing of All Human Rhinovirus Serotypes: Insights into Genus Phylogeny and Susceptibility to Antiviral Capsid-Binding Compounds", Journal of Virology, vol. 78, No. 7, (Apr. 2004), pp. 3663-3674.

Letcher, Roy M., "First Synthesis of Spiro[benzofuran-2,1'-isobenzofuran]-3,3'-dione and its X-Ray Crystal Structure", J.Chem. Soc.Perkin Trans.1, 1992, pp. 1769-1771.

Leuchs, H. et al. "New reactions of indolenines and inolinols", Justus Liebigs Annalen der Chemie, (1928), vol. 461, pp. 27-46, structures therefrom via Caplus.

Euchs, Hermann, Wulkow, Gerhard, and Gerland, Heinz, "Indolenines V. Addition of Acid Halides to Indolenines", Caplus, (1932), vol. 151, pp. 1586-1592.

Liu, Yaya et al., "Investigating the Origin of the Slow-Binding Inhibition of HCV NS3 Serine Protease by a Novel Substrate Based inhibitor", BioChemistry, vol. 42, No. 29, (Jul. 1, 2003), pp. 8862-8869.

Lombardino, J.G. et al., "Anti inflammatory 2-Aryl-1,3-indandiones", Journal of Medicinal Chemistry, (1968), vol. 11, No. 6, pp. 342-347.

(56) References Cited

OTHER PUBLICATIONS

McKinlay, Mark A. et al., "Treatment of The Picornavirus Common Cold By Inhibitors of Viral Uncoating and Attachment", Annual Review of Microbiology, (Oct. 1992), vol. 46. pp. 635-654.
Mehdi, Sayed Hansan, "Synthesis, characterization, antimicrobial and enzymatic activity of 4b,9b-dihydroxy-7,8-dihydro-4bH-indeno[1,2-b]benzofuran-9, 10(6H,9bH)-dione", Journal of Molecular Structure, 2011, vol. 1006, pp. 318-323.
Miller, F. Dewolfe et al., "Controlled Trial of Enviroxime Against Natural Rhinovirus Infections in a Community", Antimicrobial Agents and Chemotherapy, (Jan. 1985), vol. 27. No. 1, pp. 102-106.
Mosher, William A. et al., "Reactions of some methylene ketones with dimethyl phthalate. New route to 2-substituted 1,3-indandiones", The Journal of Organic Chemistry, vol. 36, No. 11, (Jun. 1, 1971), pp. 1561-1563.
Mudiganti, N.V.S., et al., "Ytterbium triflate-catalyzed conjugate addition of ß-ketoesters to activated 1,4-naphthoquinones", Tetrahedron Letters, vol. 65, (2009), pp. 1716-1723.
Na, J. E. et al., "Serendipitous one-pot synthesis of brand-new, bowl-shaped molecular architecture from bhloroglucinol and ninhydrin", Tetrahedron Letters, vol. 46, No. 26, (Jun. 27, 2005), pp. 4505-4508.
Na, Jeong Eun et al., "Selective methylation of the Ninhydrin-phenol adducts with I2 in MeOH", Bulletin of the Korean Chemical Society, vol. 25, No. 4, (2004), pp. 569-572.
Na, Jeong Eun et al., "Synthesis of benzo[b]indeno [2,1-d]furanone skeleton from ninhydrin and cyclohexane-1, 3-dione derivatives", Bulletin of the Korean Chemical Society, vol. 24, No. 12, (2003), pp. 1725-1726.
Neiland, L.E. et al., "2-Aryl-4-azaindain-1, 3-diones", Chemistry of Heterocyclic Compounds, vol. 3, No. 1, (Jan. 1, 1969), pp. 81-83.
Ooyama, Yousuke, "Molecular design of novel non-planar heteropolycyclic fluorophores with bulky substituents: convenient synthesis and solid-state fluorescence characterization", Organic & Biomolecular Chemistry, 2006, vol. 4, pp. 3406-3409.
Ozola, A. Ua et al., "A new method of synthesizing 4-azaidan-1, 3-dione derivatives", Chemistry of Heterocyclic Compounds, vol. 9, No. 8, (Aug. 1, 1973), pp. 1062.
Ozola, A. Ya et al., "4-Azaindane-1, 3-dione derivatives. III. Reactivities and prototropic transformations of new 4-azaindane-1,3-diones", Chemistry of Heterocyclic Compounds, vol. 12, No. 2, (Feb. 1, 1976), pp. 220-226.
Patick, A.K., et al, "In Vitro Antiviral Activity of AG7088, a Potent Inhibtor of Human Rhinovirus 3C Protease", Antimicrobial Agents and Chemotherapy, Oct. 1999, vol. 43, No. 10, pp. 2444-2450.
Pevear, Daniel C. et al., "Activity of Pleconaril against Enteroviruses", Antimicrobial Agents and Chemotherapy, (Sep. 1999), vol. 43, No. 9, pp. 2109-2115.
Poupelin, J.P. et al., "Derives de 1 hydroy-2 Indanedione-1, 3.II. Produits de condensation de la ninhydrine avec les polyphenols et leurs derives 0-methyles//2-hydroxy-1,3-indanedione derivatives. II. (Condensation of ninhydrin with polyphenols and their 3-methylated derivatives)", European Journal of Medicinal Chemistry, Editions Scientifique, vol. 15, No. 3, (Jan. 1, 1980), pp. 253-262.
Poupelin, Jean Pierre et al., "Synthese Et Proprietes Pharmalogiques De Derives De L'Hydroxy-2 Indanedione-1,3; I. Produits De Condensation De La Ninhydrine Avec Les Phenols C-Alkyles", Eur. J. Med. Chem.—Chimica Therapeutique, March-April, vol. 14, No. 2, (Jan. 1, 1979), pp. 171-179 (including English abstract).
Prabhakar, et al., "Identification and evaluation of antioxidant, analgesic/anti-inflammatory activity of the most active ninhydrin-phenol adducts synthesized", Bioorganic & Medicinal Chemistry, vol. 14, No. 21, (Nov. 1, 2006), pp. 7113-7120.
Registry 908828-65-9 (Sep. 27, 2006); 907954-66-9 (Sep. 20, 2006); 408315-53-7 (Apr. 26, 2002).
Rotbergs, J., et al., "Condensation of dicarboxylic acid anhydrides with compounds containing active methylene groups. XXVII. 2-Aryl-1,3-indandiones containing methyl groups," Latvijas PSR Zinatnu Akademijas Vestis, Kimijas Serija, 1974, vol. 1, pp. 75-78.
Roth, H.J., et al., "Reaktionen mit Dimethoxyanilinen und reaktiven Aromaten", Archiv der Pharmazie, (1976), vol. 82, pp. 81-91.
Schmitt, Gerard et al., "A New and Mild Synthesis of Substituted Salicylic Acids", Synthesis, vol. 1984, No. 09 (Jan. 1, 1984), pp. 758-760.
Solomek, T., et al., "Photoenolization-Induced Oxirane Ring Opening in 2,5-Dimethylbenzoyl Oxiranes To Form Pharmaceutically Promising Indanone Derivatives", J. Org. Chem. Vo. 75, No. 21, 2010, pp. 7300-7309.
Song Hyun Nam, et al., "The Reaction of Ninhydrin with Polymethylbenzenes in the Presence of Acid Catalyst: Formation of 2-aryl-1,3-indanedione and Indenoindanone Derivative", Bull. Korean Chem. Soc. vol. 20, No. 10, pp. 1229-1231, Oct. 20, 1999.
Song, H.N. et al., "Formation of Benzo[b]Indeno [2,1-d]Furanone Ring System During Alkylation of 2-(2-Hydroxyaryl)-2-Hydroxy-1,3-Indanedione Derivatives", Synthetic Communications, (1999), vol. 29, No. 16, pp. 2759-2767.
Song, Hyun Nam et al., "A Study on the Friedel-Crafts Type Reaction of Ninhydrin with Arenes", Synthetic Communications, 28(10), pp. 1865-1870, (1998).
Song, Hyun Nam et al., "Difference in Reactivity during Alkylation of 2-(2-Hydroxyaryl)-1,3-indanedione and N-(2-Hydroxyphenyl)phthalimide", Bull. Korean Chem. Soc., (1999); vol. 20, No. 6, pp. 631-632.
Song, Hyun Nam et al., "Friedel-Crafts Type Reactions of Some Activated Cyclic Ketones with Phenol Derivatives", Synthetic Communications, 29(19), pp. 3303-3311, (1999).
Song, Hyun Nam et al., "The Reaction of Ninhydrin with Trimethylbenzenes Under Friedel-Crafts Reaction Conditions", Synthetic Communications, 30(6), pp. 1057-1066, (2000).
Stadlbauer, W. et al. DN, "Thermal Cyclization of 3-Azido-2-phenyl-indan-1-one to 5H-Indeno[1,2-b]indol-10-one", Journal of Heterocyclic Chemistry, (2002) 39(1), pp. 131-135 (Abstract).
Sun, Fang-Gang, et al., "N-Heterocyclic carbine-catalyzed [4 + 1] annulation of phthalaldehyde and imines," Organic & Biomolecular Chemistry, vol. 9, No. 10, May 21, 2011, pp. 3573-3635.
Suzuki, Masaya, et al., "Photorearrangements in spiro-conjoined cyclohexa-2,5-dien-1-one", Tetrahedron vol. 67, pp. 5500-5506, Available online May 14, 2011.
The Merck Index, 2001, Thirteenth Edition, p. 674, 1380, 2432, 7314.
Thibaut et al., "A novel class of highly potent small molecule inhibitors of entero/rhinovirus replication with an excellent safety and pharmacokinetic profile are highly effective against enterovirus infections in mice.", Poster presented at 26th International Conference on Antiviral Research, San Francisco, CA, (May 11-15, 2013).
Thibaut et al., "A novel class of highly potent small molecule inhibitors of entero/rhinovirus replication that target the non-structural protein 2C", Poster presented at 26th International Conference on Antiviral Research, San Francisco, CA (May 11-15, 2013).
Timtcheva et al., "Luminescence Properties of Some 4- or 5-Aminosubstituted Indan-1,3-diones," Z. Naturforsch, (1987), vol. 42a, pp. 289-292.
Vasilev, G., et al., "Synthesis, chemical structure, and biological activity of certain N-substituted 2-ureido-or hioureido-2-phenyl-1,3-indandiones," Doklady Bolgarskoi Akademii Nauk, 1986, vol. 39, No. 2, pp. 93-96.
Vegnere, V., et al., "Adsorptive capacity of 2-amino-substituted indans on a mercury electrode," Latvijas PSR Zinatnu Akademijas Vestis, Kimijas Serija, 1973, vol. 4, pp. 446-451.
Yin-Murphy, Marguerite and Almond, Jeffrey W., "Chapter 53Picornaviruses", Medical Microbiology, 4th Ed., Galveston (TX): Univ. of Texas Medical Branch at Galveston, (1996), pp. 1-18.
Zalukaev, L.P., et al., "Synthesis of new a-nitro-a-arylmethylenephthal ides," Izvestiya Vysshikh Uchebnykh Zavedenii, Khimiya I Khimicheskaya Tekhnologiya, 1970, vol. 13, No. 10, pp. 1453-1456.
Zalukaev, L.P., et al., "Synthesis of α-nitromethylpyridine and its derivatives," Khimiya Geterotsiklicheskikh Soedinenii, 1967, vol. 3, pp. 515-517.
Zalukaievs, L., et al., "Preparation of 2-nitromethylquinoline and its derivatives," Zhurnal Obshchei Khimii, 1956, vol. 26, pp. 2639-2642.

(56) References Cited

OTHER PUBLICATIONS

Zalukajevs, L., et al., "Nitration of phthalones," Zhurnal Obshchei Khimii, 1957, vol. 27, pp. 3278-3282.

Blood et al., "The Preparation of 4 : 4'-Bistetrahydropyranyl and of Ethane-1 : 1 : 2 : 2-tetra-acetic Acid," Journal of Chemical Society, 1952, pp. 2268-2272.

Cheng et al., "N-Heterocyclic Carbene Catalyzed Reaction of Phthalaldehydes: Controllable Stereoselective Synthesis of Polyhydroxylated Spiro- and Fused Indenones Dictated by the Structure of NHC Catalysts," The Journal of Organic Chemistry, 2011, vol. 76, pp. 1844-1851.

* cited by examiner

ANTIVIRAL 1,3-DI-OXO-INDENE COMPOUNDS

CROSS REFERENCE TO RELATED APPLICATIONS

This application claims priority to U.S. Provisional Application No. 63/012,770, filed Apr. 20, 2020, the disclosure of which is hereby incorporated by reference in its entirety for all purposes.

FIELD OF THE INVENTION

The present invention relates to novel 1,3-dioxoindene compounds that are inhibitors of picornaviruses including coxsackie-, entero-, echo-, polio-, and rhinoviruses, and are thus useful to treat viral infections, including poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, cold, herpangina, foot-and-mouth disease, asthma, chronic obstructive pulmonary disease, pneumonia, sinusitis or otitis media. The invention provides novel tetracyclic pyridone compounds as disclosed herein, pharmaceutical compositions containing such compounds, and methods of using these compounds and compositions in the treatment and prevention of viral diseases.

BACKGROUND

Picornaviruses are non-enveloped, positive single-stranded RNA viruses with an RNA genome 7.2-8.5 Kb long. These viruses are very small and globular in shape with a size of about 22-30 nm, and were rust identified a long time ago. Among the viruses belonging to the family Picornaviridae are enteroviruses including rhinovirus, poliovirus, coxsackievirus A, coxsackievirus B. and echovirus, and hepatitis A virus.

The diseases that picornaviruses cause are varied, ranging from respiratory diseases to digestive diseases, to circulatory diseases and to dermal diseases, examples of which include poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, cold, herpangina, and foot-and-mouth disease. However, there are no therapeutics for curing these diseases. Most of the drugs under development are uncoating inhibitors. Viruses belonging to the family Picornaviridae cause various diseases including the aforementioned respiratory diseases, which evoke hygienic, social and economic issues. Picornaviruses are the main causative agents of waterborne diseases. Being very stable and difficult to disinfect, the RNA viruses incessantly cause related diseases.

Human rhinoviruses (hRV) have been recently associated with the majority of asthma exacerbations, and are known to exist even in bronchial tissues of many stable asthma patients. Comparison of respective bronchial mucosa biopsy specimens taken from asthma and non-asthma patients showed significantly higher frequencies of detection of human rhinoviruses in the lower respiratory tract of asthma patients, compared to non-asthma patients. It has also been reported that there is correlation between the presence of human rhinovirus and the clinical severity of asthma. In addition, rhinoviruses cause chronic obstructive pulmonary disease, pneumonia, sinusitis, and otitis media as well as asthma.

Rhinoviruses are the main causative of the common cold while enterovirus-induced diseases include meningitis, respiratory tract infection, etc. Extensive effort to provide vaccination against poliovirus has significantly reduced the onset of poliomyelitis worldwide, but there are still reports of cases of the disease in Niger, Nigeria, Egypt, India, Pakistan, and Afghanistan, Hepatitis A is now possible to control to some degree thanks to vaccines for hepatitis A viruses. However, no vaccines for coxsackieviruses, echoviruses, or rhinoviruses have been developed, thus far.

Particularly, coxsackievirus B is a main cause of myocarditis, which may develop, in serious cases, into idiopathic dilated cardiomyopathy, which requires heart transplantation.

Enviroxime derivatives are considered the most promising candidate with a broad anti-enterovirus- and anti-rhinovirus activity. Enviroxime interferes with the synthesis of plus-strand RNA by binding to the virus protein 3A that is required for the formation of RNA intermediates in the virus reproduction (Heinz B A and Vance L M: J Virol, 1995, 69(7), 4189-97). In clinical studies, however, the compound was observed to have insignificant or few therapeutic effects, with the concomitant detection of bad pharmacokinetics and unwanted side effects (Miller F D et al.: Antimicrob Agents Chemother. 1985, 27(1), 102-6).

The protease inhibitor AG 7088 has been developed on the basis of the knowledge about the fine structure and function of the viral protease 2C. In the cell culture in the nanomolar concentration range. AG 7088 has an effect against 48 rhinovirus types and coxsackievirus A21. B3, enterovirus 70 and echovirus 11 (Pattick A K et al.: Antimicrobila Agents Chemother, 1999, 43(10), 2444-50).

Thanks to the clarification of the molecular structure of the viral capsids, the preconditions for a purposeful design of capsid blockers, the "WIN substances", have been obtained (Diana G D: Curr Med Chem 2003, 2, 1-12). They inhibit the adsorption and/or the uncoating of rhinoviruses and enteroviruses. Some of the WIN substances have a highly specific effect only against individual genera or virus types of the picornaviruses. Other derivatives inhibit the replication both of rhinoviruses and enteroviruses. Arildone, disoxaril and pirodavir belong, for example, to the WIN substances. These compounds showed very good antiviral effects in the cell culture. However, a poor solubility (arildone), low bioavailability (arildone and disoxaril), a rapid metabolization and excretion (disoxaril and WIN 54954) as well as side effects, such as skin rash (WIN 54954), made a clinical application impossible.

Pleconaril, a kind of WIN substance, has a very good oral bioavailability and after its binding to the hydrophobe pocket in the viruscapsid, it inhibits the penetration of rhino-, echo- and coxsackieviruses (Pevear D C et al.: Antimicrob Agents Chemother 1999, 43(9), 2109-15; McKinlay M A et al.: Annu Rev Microbiol 1992, 46, 635-54). Therefore, pleconaril is potentially effective against a broad spectrum of virus diseases, ranging from the common cold to the viral meningitis or myocarditis. Resistances were observed for rhinoviruses, enterovirus 71 and coxsackievirus B3 (Ledford R M et al.: J Virol 2004, 78(7), 3663-74; Groarke J M et al.: J Infect Dis 1999, 179(6), 1538-41). However, the proven therapeutic effect was not sufficient for the registration of pleconaril (Picovir, Viropharma. USA) as an agent for the treatment of rhinovirus infections in the USA. In March 2002, a corresponding application was refused by the Food and Drug Administration (FDA) because therapy success was too low and side effects were observed.

BTA-798 was found to have higher antiviral activity than pleconaril, as evaluated in vitro and in vivo with rhinoviruses, and is now being under a clinical test (Ryan. J. et al. Antiviral Res [18th Intl Conf Antiviral Res (April 11-14. Barcelona) 2005] 2005, 65(3): Abst LB-11).

However, no antiviral drugs that have gained approval for use in the treatment of entero- or rhinoviruses have been developed, so far. There remains a need for new treatments and therapies against entero- or rhinoviruses.

Leading to the present invention, intensive and thorough research into effective virustatics against picornaviruses including coxsackie-, entero-, echo-, polio-, and rhinoviruses, culminated in the finding that novel 1,3-Dioxoindene derivatives exhibit highly inhibitory activity against picornaviruses including coxsackie-, entero-, echo-, polio-, and rhinoviruses.

SUMMARY

The present invention provides compounds with antiviral activity. The invention also provides pharmaceutical compositions containing the compounds as well as methods to using the compounds and compositions to inhibit virus replication or reactivation, and to treat disease conditions associated with or caused by viruses. Further objects of this invention are described in the following description and the examples.

In one aspect, the invention provides compounds of Formula (I):

[I]

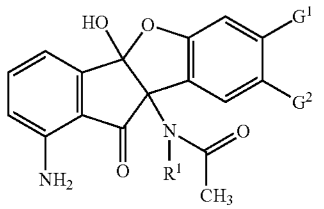

wherein, one of $G^1$ and $G^2$ is selected from linear or branched $C_1$-$C_5$alkyl; linear or branched $C_1$-$C_5$alkyloxy; linear or branched $C_1$-$C_5$haloalkyl; linear or branched $C_1$-$C_5$haloalkyloxy; halo and 3-7 membered cycloalkyl; the other of $G^1$ and $G^2$ is H; and $R^1$ is selected from H and linear or branched $C_1$-$C_5$alkyl; and optionally, the compound is in an enantiomerically pure form. In another aspect, the invention provides a pharmaceutical composition comprising a therapeutically effective amount of a compound of the present invention and one or more pharmaceutically acceptable carriers. In another aspect, the invention provides a combination, in particular a pharmaceutical combination, comprising a therapeutically effective amount of compound of the present invention and one or more therapeutically active agents.

DETAILED DESCRIPTION

For purposes of interpreting this specification, the following definitions will apply, and whenever appropriate, terms used in the singular will also include the plural.

Terms used in the specification have the following meanings unless the context clearly indicates otherwise:

As used herein, the term "subject" refers to an animal. In certain aspects, the animal is a mammal. A subject also refers to for example, primates (e.g., humans), cows, sheep, goats, horses, dogs, cats, rabbits, rats, mice, fish, birds and the like. In certain embodiments, the subject is a human. A "patient" as used herein refers to a human subject. As used herein, a subject is "in need of" a treatment if such subject would benefit biologically, medically or in quality of life from such treatment.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

"Halo" or "halogen", as used herein, may be fluorine, chlorine, bromine or iodine.

"$C_{1-6}$ alkyl" or "$C_1$-$C_6$ alkyl", as used herein, denotes straight chain or branched alkyl having 1-6 carbon atoms. If a different number of carbon atoms is specified, such as $C_4$ or $C_3$, then the definition is to be amended accordingly, such as "$C_{1-4}$ alkyl" will represent methyl, ethyl, propyl, isopropyl, butyl, isobutyl, sec-butyl and tert-butyl.

"$C_{1-6}$ alkoxy", as used herein, denotes straight chain or branched alkoxy (—O—Alkyl) having 1-6 carbon atoms. If a different number of carbon atoms is specified, such as $C_4$ or $C_3$, then the definition is to be amended accordingly, such as "$C_{1-4}$ alkoxy" will represent methoxy, ethoxy, propoxy, isopropoxy, butoxy, isobutoxy, sec-butoxy and tert-butoxy.

"$C_{1-4}$ Haloalkyl" or "$C_1$-$C_4$ haloalkyl" as used herein, denotes straight chain or branched alkyl having 1-4 carbon atoms wherein at least one hydrogen has been replaced with a halogen. The number of halogen replacements can be from one up to the number of hydrogen atoms on the unsubstituted alkyl group. If a different number of carbon atoms is specified, such as $C_6$ or $C_3$, then the definition is to be amended accordingly. Thus "$C_1$a haloalkyl" will represent methyl, ethyl, propyl, isopropyl, butyl, isobutyl, sec-butyl and tert-butyl that have at least one hydrogen substituted with halogen, such as where the halogen is fluorine: $CF_3CF_2$—, $(CF_3)_2CH$—, $CH_3$—$CF_2$—, $CF_3CF_2$—, $CF_3$, $CF_2H$—, $CF_3CF_2CH(CF_3)$— or $CF_3CF_2CF_2CF_2$—.

"$C_3$ cycloalkyl" as used herein refers to a saturated monocyclic hydrocarbon ring of 3 to 8 carbon atoms.

Examples of such groups include cyclopropyl, cyclobutyl, cyclopentyl and cyclohexyl. If a different number of carbon atoms is specified, such as $C_3$-$C_6$, then the definition is to be amended accordingly.

Various embodiments of the invention are described herein. It will be recognized that features specified in each embodiment may be combined with other specified features to provide further embodiments. The following enumerated embodiments are representative of the invention:

Embodiment 1. A compound of formula I, or a pharmaceutically acceptable salt thereof:

[I]

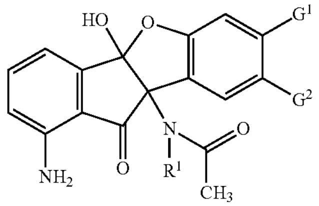

wherein, one of $G^1$ and $G^2$ is selected from linear or branched $C_1$-$C_5$ alkyl; linear or branched $C_1$-$C_5$ alkyloxy; linear or branched $C_1$-$C_5$ haloalkyl; linear or branched $C_1$-$C_5$ haloalkyloxy; halo and 3-7 membered cycloalkyl; and the other of $G^1$ and $G^2$ is H; and $R^1$ is selected from H and linear or branched $C_1$-$C_5$alkyl.

Embodiment 2. The compound of Embodiment 1, or the pharmaceutically acceptable salt thereof, wherein $G^1$ is selected from linear or branched $C_1$-$C_5$ haloalkyl; linear or branched $C_1$-$C_5$ haloalkyloxy; and 3-7 membered cycloalkyl.

Embodiment 3. The compound of Embodiment 1 or Embodiment 2, or the pharmaceutically acceptable salt thereof, wherein $G^1$ is linear or branched $C_1$-$C_5$ haloalkyl.

Embodiment 4. The compound of any one of Embodiments 1 to 3, or the pharmaceutically acceptable salt thereof, wherein $G^1$ is $CF_3$.

Embodiment 5. The compound of Embodiment 1 or Embodiment 2, or the pharmaceutically acceptable salt thereof, wherein $G^1$ is linear or branched $C_1$-$C_5$ haloalkyloxy.

Embodiment 6. The compound of any one of Embodiments 1, 2, and 5, or the pharmaceutically acceptable salt thereof, wherein $G^1$ is $OCF_3$.

Embodiment 7. The compound of Embodiment 1 or Embodiment 2, or the pharmaceutically acceptable salt thereof, wherein $G^1$ is 3-7 membered cycloalkyl.

Embodiment 8. The compound of any one of Embodiments 1, 2, and 7, or the pharmaceutically acceptable salt thereof, wherein $G^1$ is cyclopropyl.

Embodiment 9. The compound of and one of Embodiments 1 to 8, or the pharmaceutically acceptable salt thereof, wherein $G^2$ is H.

Embodiment 10. The compound of Embodiment 1 or Embodiment 9, or the pharmaceutically acceptable salt thereof, wherein $G^1$ is methyl.

Embodiment 11. The compound of Embodiment 1 or Embodiment 9, or the pharmaceutically acceptable salt thereof, wherein $G^1$ is $OCH_3$.

Embodiment 12. The compound of Embodiment 1 or Embodiment 9, or the pharmaceutically acceptable salt thereof, wherein $G^1$ is isopropyl.

Embodiment 13. The compound of Embodiment 1 or Embodiment 9, or the pharmaceutically acceptable salt thereof, wherein $G^1$ is halo.

Embodiment 14. The compound of Embodiment 1, or the pharmaceutically acceptable salt thereof, wherein $G^1$ is H.

Embodiment 15. The compound of Embodiment 1, or the pharmaceutically acceptable salt thereof, wherein $G^2$ is methyl.

Embodiment 16. The compound of any one of Embodiments 1 to 15, or a pharmaceutically acceptable salt thereof, wherein the compound is of Formula (II):

[II]

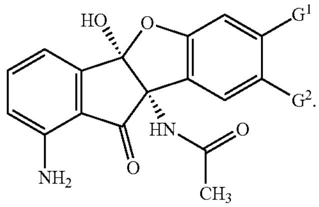

Embodiment 17. The compound of any one of Embodiments 1 to 10 and 12 to 13, or a pharmaceutically acceptable salt thereof, having Formula (III):

[III]

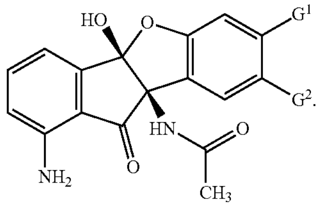

Embodiment 17a. The compound of any one of Embodiments 1 to 9, or a pharmaceutically acceptable salt thereof, wherein the compound is of Formula (IV):

[IV]

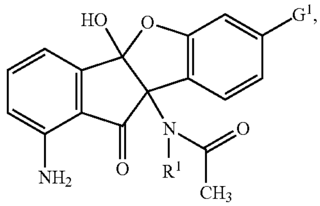

wherein $G^1$ is selected from linear or branched $C_1$-$C_5$ haloalkyl; linear or branched $C_1$-$C_5$ haloalkyloxy; and 3-7 membered cycloalkyl.

Embodiment 17b. The compound of any one of Embodiments 1 to 9 and 17a, wherein $G^1$ is selected from $CF_3$, $OCF_3$, and cyclopropyl.

Embodiment 17c. The compound of any one of Embodiments 1 to 9, 17a, and 17b, wherein $R^1$ is selected from H and methyl.

Embodiment 18. The compound of any one of Embodiments 1 to 17, selected from:
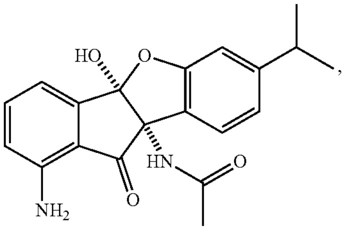
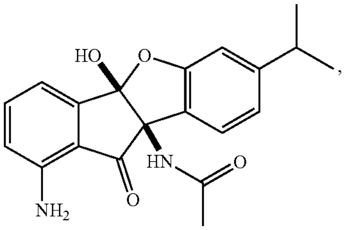
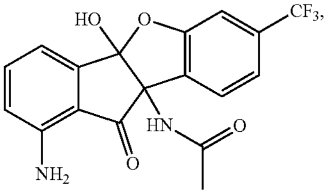
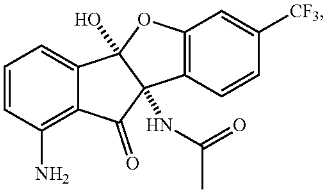
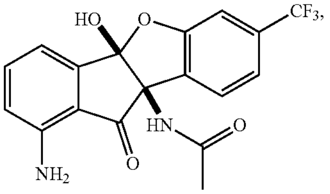
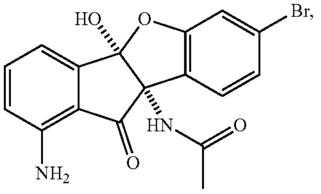
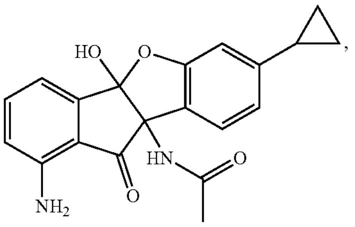
-continued
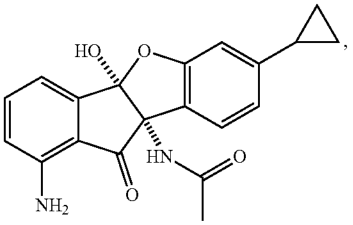
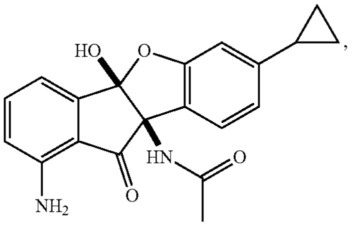
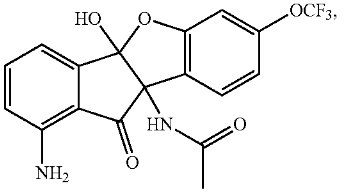
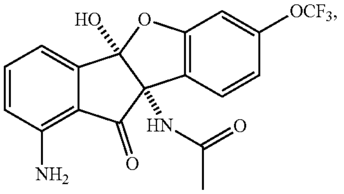
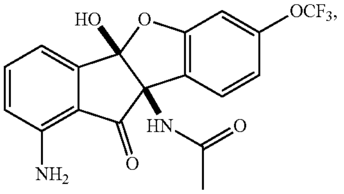
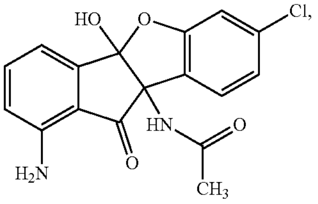
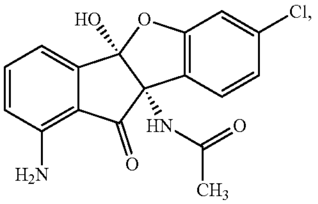
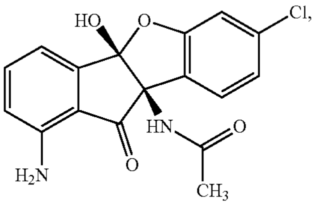

-continued

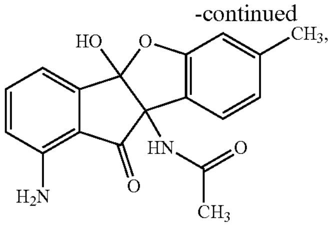

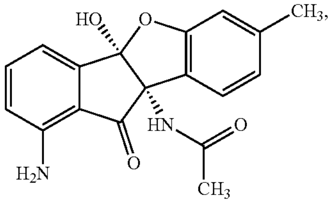

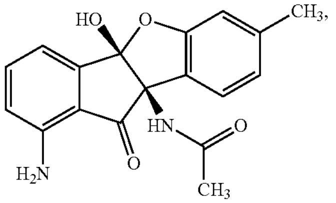

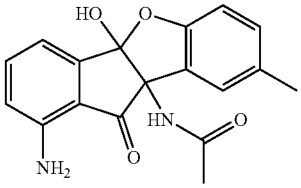

,

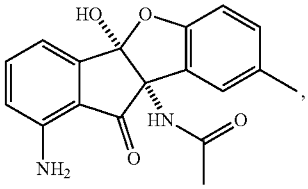

,

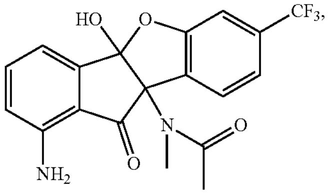

and

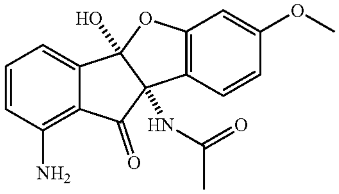

, or a pharmaceutically acceptable salt thereof.

Embodiment 18a. A compound, or pharmaceutically acceptable salt thereof, or optical isomer thereof, selected from the group consisting of: N-((4bR,9bR)-1-amino-4b-hydroxy-7-isopropyl-10-oxo-4b,10-dihydro-9bH-indeno[1,2-b]benzofuran-9b-yl)acetamide; N-(1-amino-4b-hydroxy-10-oxo-7-(trifluoromethyl)-4b,10-dihydro-9bH-indeno[1,2-b]benzofuran-9b-yl)acetamide (19); N-((4bR,9bR)-1-amino-4b-hydroxy-10-oxo-7-(trifluoromethyl)-4b,10-dihydro-9bH-indeno[1,2-b]benzofuran-9b-yl)acetamide; N-((4bS,9bS)-1-amino-4b-hydroxy-10-oxo-7-(trifluoromethyl)-4b,10-dihydro-9bH-indeno[1,2-b]benzofuran-9b-yl)acetamide; N-((4bR,9bR)-1-amino-7-bromo-4b-hydroxy-10-oxo-4b,10-dihydro-9bH-indeno[1,2-b]benzofuran-9b-yl)acetamide; N-(1-amino-7-cyclopropyl-4b-hydroxy-10-oxo-4b,10-dihydro-9bH-indeno[1,2-b]benzofuran-9b-yl)acetamide; N-((4bR,9bR)-1-amino-7-cyclopropyl-4b-hydroxy-10-oxo-4b,10-dihydro-9bH-indeno[1,2-b]benzofuran-9b-yl)acetamide; N-((4bS,9bS)-1-amino-7-cyclopropyl-4b-hydroxy-10-oxo-4b,10-dihydro-9bH-indeno[1,2-b]benzofuran-9b-yl)acetamide; N-(1-amino-4b-hydroxy-10-oxo-7-(trifluoromethoxy)-4b,10-dihydro-9bH-indeno[1,2-b]benzofuran-9b-yl)acetamide; N-((4bR,9bR)-1-amino-4b-hydroxy-10-oxo-7-(trifluoromethoxy)-4b,10-dihydro-9bH-indeno[1,2-b]benzofuran-9b-yl)acetamide; N-((4bS,9bS)-1-amino-4b-hydroxy-10-oxo-7-(trifluoromethoxy)-4b,10-dihydro-9bH-indeno[1,2-b]benzofuran-9b-yl)acetamide; N-(1-amino-7-chloro-4b-hydroxy-10-oxo-4b,10-dihydro-9bH-indeno[1,2-b]benzofuran-9b-yl)acetamide; N-((4bR,9bR)-1-amino-7-chloro-4b-hydroxy-10-oxo-4b,10-dihydro-9bH-indeno[1,2-b]benzofuran-9b-yl)acetamide; N-((4bS,9bS)-1-amino-7-chloro-4b-hydroxy-10-oxo-4b,10-dihydro-9bH-indeno[1,2-b]benzofuran-9b-yl)acetamide; N-(1-amino-4b-hydroxy-7-methyl-10-oxo-4b,10-dihydro-9bH-indeno[1,2-b]benzofuran-9b-yl)acetamide; N-((4bR,9bR)-1-amino-4b-hydroxy-7-methyl-10-oxo-4b,10-dihydro-9bH-indeno[1,2-b]benzofuran-9b-yl)acetamide and N-((4bS,9bS)-1-amino-4b-hydroxy-7-methyl-10-oxo-4b,10-dihydro-9bH-indeno[1,2-b]benzofuran-9b-yl)acetamide; N-(1-amino-4b-hydroxy-8-methyl-10-oxo-4b,10-dihydro-9bH-indeno[1,2-b]benzofuran-9b-yl)acetamide; N-((4bR,9bR)-1-amino-4b-hydroxy-8-methyl-10-oxo-4b,10-dihydro-9bH-indeno[1,2-b]benzofuran-9b-yl)acetamide; N-(1-amino-4b-hydroxy-10-oxo-7-(trifluoromethyl)-4b,10-dihydro-9bH-indeno[1,2-b]benzofuran-9b-yl)-N-methylacetamide; N-((4bR,9bR)-1-amino-4b-hydroxy-7-methoxy-10-oxo-4b,10-dihydro-9bH-indeno[1,2-b]benzofuran-9b-yl)acetamide; or a pharmaceutically acceptable salt thereof.

Embodiment 18b. The compound of Embodiment 1, which is

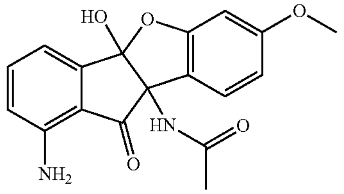

or

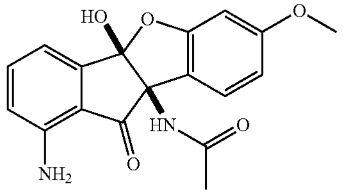

, or a pharmaceutically acceptable salt thereof.

Embodiment 19. The compound of any one of Embodiments 1 to 18, a pharmaceutically acceptable salt thereof or optical isomer thereof for prevention or treatment of a viral disease.

Embodiment 20. A pharmaceutical composition for prevention or treatment of a viral disease, comprising the compound any one of Embodiments 1 to 18, a pharmaceutically acceptable salt thereof or optical isomer thereof and a pharmaceutically acceptable diluent or excipient.

Embodiment 21. A combination comprising a compound according to any one of Embodiments 1 to 18 or a pharmaceutically acceptable salt thereof or a pharmaceutical composition as set forth in Embodiment 20 and one or more therapeutically active agents.

Embodiment 22. A method of treating a viral disease comprising administering to a subject a therapeutically effective amount of a compound according to any one of Embodiments 1 to 18 or a pharmaceutically acceptable salt thereof or a pharmaceutical composition as set forth in Embodiment 20 or a combination as set forth in Embodiment 21.

Embodiment 23. Use of a compound of Embodiment 19 or a pharmaceutically acceptable salt thereof or optical isomer thereof or a pharmaceutical composition as set forth in Embodiment 20, or a combination as set forth in Embodiment 21 for the prevention or treatment of a viral disease.

Embodiment 24. The compound of Embodiment 19 or a pharmaceutical composition as set forth in Embodiment 20, or a method as set forth in Embodiment 21, or a use as set forth in Embodiment 23, wherein the viral disease is caused by coxsackievirus.

Embodiment 25. The compound of Embodiment 19 or a pharmaceutical composition as set forth in Embodiment 20, or a method as set forth in Embodiment 21, or a use as set forth in Embodiment 23, wherein the viral disease is caused by poliovirus.

Embodiment 26. The compound of Embodiment 19 or a pharmaceutical composition as set forth in Embodiment 20, or a method as set forth in Embodiment 21, or a use as set forth in Embodiment 23, wherein the viral disease is caused by echovirus.

Embodiment 27. The compound of Embodiment 19 or a pharmaceutical composition as set forth in Embodiment 20, or a method as set forth in Embodiment 21, or a use as set forth in Embodiment 23, wherein the viral disease is caused by enterovirus.

Embodiment 28. The compound of Embodiment 19 or a pharmaceutical composition as set forth in Embodiment 20, or a method as set forth in Embodiment 21, or a use as set forth in Embodiment 23, wherein the viral disease is caused by rhinovirus.

Embodiment 29. The compound of Embodiment 19 or a pharmaceutical composition as set forth in Embodiment 20, or a method as set forth in Embodiment 21, or a use as set forth in Embodiment 23, wherein the viral disease is caused by picornavirus.

Embodiment 30. The compound of Embodiment 19 or a pharmaceutical composition as set forth in Embodiment 20, or a method as set forth in Embodiment 21, or a use as set forth in Embodiment 23, wherein the viral disease is poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, flu, herpangina, foot-and-mouth disease, asthma, chronic obstructive pulmonary disease, pneumonia, sinusitis or otitis media.

The compound of Formula I, II, or III are novel and useful as intermediates for preparation of the compounds of Formula (I)-(III) described herein.

Another embodiment of the invention provides a compound as described above, or a pharmaceutically acceptable salt thereof, as a medicament.

Also within the scope of this invention is the use of a compound of Formula I, II, or III, or a pharmaceutically acceptable salt thereof, for the manufacture of a medicament for the treatment or prevention of a viral disease and/or infection in a human being.

Included within the scope of this invention is a pharmaceutical composition comprising a compound of Formula I, II, or III, or a pharmaceutically acceptable salt thereof, and a pharmaceutically acceptable carrier.

According to a further aspect of this embodiment the pharmaceutical composition according to this invention further comprises a therapeutically effective amount of at least one other antiviral agent.

The invention also provides the use of a pharmaceutical composition as described hereinabove for the treatment of a virus infection in a human being having or at risk of having the infection.

The invention also provides the use of a pharmaceutical composition as described hereinabove for the treatment of viral disease or infection in a human being having or at risk of having the disease.

Another aspect of the invention involves a method of treating or preventing a viral disease and/or infection in a human being by administering to the human being an antivirally effective amount of a compound of the invention, a pharmaceutically acceptable salt thereof, or a composition as described above, alone or in combination with at least one other antiviral agent, administered together or separately.

An additional aspect of this invention refers to an article of manufacture comprising a composition effective to treat a viral disease and/or infection; and packaging material comprising a label which indicates that the composition can be used to treat disease and/or infection by a virus; wherein the composition comprises a compound of Formula I, II, or III according to this invention or a pharmaceutically acceptable salt thereof.

Still another aspect of this invention relates to a method of inhibiting the replication of a virus, comprising exposing the virus to an effective amount of the compound of Formula I, II, or III, or a salt thereof, under conditions where replication of the virus is inhibited. This method can be practiced in vitro or in vivo.

Further included in the scope of the invention is the use of a compound of Formula I, II, or III, or a salt thereof, to inhibit the replication of a virus.

In one embodiment, the invention provides a pharmaceutical composition comprising a compound of the present invention and another therapeutic agent(s). Optionally, the pharmaceutical composition may comprise a pharmaceutically acceptable carrier, as described above. In some embodiments, the compound of Formula I, II, or III is co-administered with at least one additional agent selected from: a virus inhibitor or vaccine.

These additional agents may be combined with the compounds of this invention to create a single pharmaceutical dosage form. Alternatively, these additional agents may be separately administered to the patient as part of a multiple dosage form, for example, using a kit. Such additional agents may be administered to the patient prior to, concurrently with, or following the administration of a compound of the invention, or a pharmaceutically acceptable salt thereof.

The dose range of the compounds of the invention applicable per day is usually from 0.01 to 100 mg/kg of body weight, sometimes from 0.1 to 50 mg/kg of body weight. Each dosage unit may conveniently contain from 5% to 95% active compound (w/w). Sometimes such preparations contain from 20% to 80% active compound.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

When the composition of this invention comprises a combination of a compound of the invention and one or more additional therapeutic or prophylactic agent, both the compound and the additional agent may be present at dosage levels of between about 10 to 100%, e.g. between about 10 and 80% of the dosage normally administered in a monotherapy regimen.

Antiviral agents contemplated for use in such combination therapy include agents (compounds or biologicals) that are effective to inhibit the formation and/or replication of a virus in a human being, including but not limited to agents that interfere with either host or viral mechanisms necessary for the formation and/or replication of a virus in a human being.

Many compounds of the invention contain one or more chiral centers. These compounds may be made and used as single isomers or as mixtures of isomers. Methods for separating the isomers, including diastereomers and enantiomers, are known in the art, and examples of suitable methods are described herein. In certain embodiments, the compounds of the invention are used as a single substantially pure isomer, meaning at least 90% of a sample of the compound is the specified isomer and less than 10% of the sample is any other isomer or mixture of isomers. In some embodiments, at least 95% of the sample is a single isomer. Where in vitro activity differences between isomers are relatively small, e.g. less than about a factor of 4, a single isomer may be selected based on activity level against viral replication in cell culture, using methods such as those described herein: the isomer having a lower IC-50 or EC-50 may be selected.

The compounds of the invention may be synthesized by the general synthetic routes below, specific examples of which are described in more detail in the Examples.

The invention also provides methods of making compounds of Formula I, II, or III as described herein and intermediates useful for preparation of compounds of Formula I, II, or III.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

The term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible stereoisomers, including racemic mixtures, diastereomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any resulting mixtures of isomers can be separated on the basis of the physicochemical differences of the constituents, into the pure or substantially pure geometric or optical isomers or diastereomers, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

As used herein, the terms "salt" or "salts" refers to an acid addition or base addition salt of a compound of the present invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is intended to represent unlabeled forms as well as isotopically labeled forms of the compounds of the present invention having up to three atoms with non-natural isotope distributions, e.g., sites that are enriched in deuterium or $^{13}C$ or $^{15}N$. Isotopically labeled compounds have structures depicted by the formulas given herein except that one or more atoms are replaced by an atom having a selected atomic mass or mass number other than the natural-abundance mass distribution. Examples of isotopes that can be usefully over-incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds of the present invention, for example those into which radioactive isotopes, such as $^{3}H$ and $^{14}C$, or those in which non-radioactive isotopes, such as $^{2}H$ and $^{13}C$ are present at levels substantially above normal isotope distribution. Such isotopically labelled compounds are useful in metabolic studies (with $^{14}C$, for example), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound of the present invention may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent typically employed. Labeled samples may be useful with quite low isotope incorporation, such as where a radiolabel is used to detect trace amounts of the compound.

Further, more extensive substitution with heavier isotopes, particularly deuterium (i.e., $^{2}H$ or D), may afford certain therapeutic advantages resulting from greater metabolic stability, for example increased in vivo half-life or reduced dosage requirements or an improvement in therapeutic index. It is understood that deuterium in this context is regarded as a substituent of a compound of the present invention, and typically a sample of a compound having deuterium as a substituent has at least 50% deuterium incorporation at the labeled position(s). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d^6$-acetone, $d^6$-DMSO.

Compounds of the present invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The compounds of the invention can be administered by known methods, including oral, parenteral, inhalation, and the like. In certain embodiments, the compound of the invention is administered orally, as a pill, lozenge, troche, capsule, solution, or suspension. In other embodiments, a compound of the invention is administered by injection or infusion. Infusion is typically performed intravenously, often over a period of time between about 15 minutes and 4 hours. In other embodiments, a compound of the invention is administered intranasally or by inhalation; inhalation methods are particularly useful for treatment of respiratory infections. Compounds of the present invention exhibit oral bioavailability, so in some embodiments, the compounds may be administered orally.

A compound of the present invention may also be used in combination with other agents (combination partners), e.g., an additional antiviral agent that is or is not of the formula I, for treatment of a viral infection in a subject.

By the term "combination", is meant either a fixed combination in one dosage unit form, as separate dosage forms suitable for use together either simultaneously or sequentially, or as a kit of parts for the combined administration where a compound of the present invention and a combination partner may be administered independently at the same time or separately within time intervals that especially allow that the combination partners show a cooperative, e.g., synergistic, effect, or any combination thereof.

In certain embodiments of the present invention, a compound of the present invention is used in combination with a second antiviral agent, such as those named herein.

The second antiviral agent may be administered in combination with the compounds of the present inventions wherein the second antiviral agent is administered prior to, simultaneously, or after the compound or compounds of the present invention. When simultaneous administration of a compound of the invention with a second agent is desired and the route of administration is the same, then a compound of the invention may be formulated with a second agent into the same dosage form. An example of a dosage form containing a compound of the invention and a second agent is a tablet or a capsule.

In some embodiments, a combination of a compound of the invention and a second antiviral agent may provide synergistic activity. The compound of the invention and second antiviral agent may be administered together, separate but simultaneously, or sequentially.

An "effective amount" of a compound is that amount necessary or sufficient to treat or prevent a viral infection and/or a disease or condition described herein. In an example, an effective amount of a viral inhibitor of Formula I is an amount sufficient to treat viral infection in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a viral infection. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical compositions for use in the treatment of these diseases. The invention provides methods of use of compounds of the present invention in the treatment of these diseases or for preparation of pharmaceutical compositions having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (sometimes, 0.5 to 90%) of at least one compound of Formula (I) or any subgenus thereof as active ingredient in combination with a pharmaceutically acceptable carrier, or optionally two or more pharmaceutically acceptable carriers.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Typically, pharmaceutically acceptable carriers are sterilized and/or substantially pyrogen-free.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, inhalation, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, sometimes from about 5 percent to about 70 percent, sometimes from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored base, for example, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or e.g., in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration may comprise one or more compounds of the invention in combination with one or more pharmaceutically acceptable carriers such as sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, glycol ethers, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Intravenous infusion is sometimes a method of delivery for compounds of the invention. Infusion may be used to deliver a single daily dose or multiple doses. In some embodiments, a compound of the invention is administered by infusion over an interval between 15 minutes and 4 hours, typically between 0.5 and 3 hours. Such infusion may be used once per day, twice per day or up to three times per day.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated effects, will range from about 0.0001 to about 100 mg per kilogram of body weight per day, sometimes from about 0.01 to about 50 mg per kg per day, and sometimes from about 0.1 to about 20 mg per kg per day. An effective amount is that amount which prevents or treats a viral infection.

If desired, the effective daily dose of the active compound may be administered as a single dose per day, or as two, three, four, five, six or more sub-doses administered separately at appropriate intervals throughout the day, optionally, in unit dosage forms. Compounds delivered orally or by inhalation, are commonly administered in one to four doses per day. Compounds delivered by injection are typically administered once per day, or once every other day. Compounds delivered by infusion are typically administered in one to three doses per day. When multiple doses are administered within a day, the doses may be administered at intervals of about 4 hours, about 6 hours, about 8 hours or about 12 hours.

While it is possible for a compound of the present invention to be administered alone, it is possible to administer the compound as a pharmaceutical composition such as those described herein. Thus methods of using the compounds of the invention include administering the compound as a pharmaceutical composition, wherein at least one compound of the invention is admixed with a pharmaceutically acceptable carrier prior to administration.

General Synthetic Procedures

The compounds as described herein may be synthesized by the general synthetic routes below, specific examples of which are described in more detail in the Examples.

All starting materials, building blocks, reagents, acids, bases, dehydrating agents, solvents, and catalysts utilized to synthesize the compounds of the invention are either commercially available or can be produced by organic synthesis methods known to one of ordinary skill in the art (Houben-Weyl 4th Ed. 1952, Methods of Organic Synthesis, Thieme, Volume 21).

LIST OF ABBREVIATIONS

Ac acetyl
ACN or MeCN Acetonitrile
AcOEt/EtOAc Ethyl acetate
AcOH acetic acid
Aq aqueous
Bn benzyl
Bu butyl (nBu=n-butyl, tBu=tert-butyl)
CDI Carbonyldiimidazole
$CH_3CN$ Acetonitrile
DBU 1,8-Diazabicyclo[5.4.0]-undec-7-ene
$Boc_2O$ di-tert-butyl dicarbonate
DCE 1,2-Dichloroethane
DCM Dichloromethane
DIAD Diisopropyl azodicarboxylate
DiBAl-H Diisobutylaluminum Hydride
DIPEA or DIEA N-Ethyldiisopropylamine
DMA N,N-dimethylacetamide
DMAP Dimethylaminopyridine
DMF N,N-Dimethylformamide
DMSO Dimethylsulfoxide
EDC 1-Ethyl-3-(3-dimethylaminopropyl)carbodiimide
EI Electrospray ionisation
$Et_2O$ Diethylether
$Et_3N$ Triethylamine
Ether Diethylether
EtOAc or EA Ethyl acetate
EtOH Ethanol
FC Flash Chromatography
h hour(s)
HATU O-(7-Azabenzotriazole-1-yl)-N,N,N'N'-tetramethyluronium hexafluorophosphate
HBTU O-(Benzotriazol-1-yl)-N,N,N',N'-tetramethyluronium hexafluorophosphate
HCl Hydrochloric acid
HMPA Hexamethylphosphoramide
HOBt 1-Hydroxybenzotriazole
HPLC High Performance Liquid Chromatography
$H_2O$ Water
IPA isopropanol
L liter(s)
LC-MS Liquid Chromatography Mass Spectrometry
LiHMDS Lithium bis(trimethylsilyl)amide
$MgSO_4$ Magnesium Sulfate
Me methyl
Mel Iodomethane
MeOH Methanol
mg milligram
min minute(s)
mL milliliter
MS Mass Spectrometry
MsCl methanesulfonyl chloride
$NaHCO_3$Sodium Bicarbonate
$Na_2SO_4$ Sodium Sulfate $NH_2OH$ hydroxylamine
Pd/C palladium on charcoal
$Pd(OH)_2$ palladium hydroxide
PG protecting group
Ph phenyl
$Ph_3P$ triphenyl phosphine
Prep Preparative
Rf ratio of fronts
RP reverse phase
Rt Retention time
RT Room temperature
SFC Supercritical Fluid Chromatography
$SiO_2$ Silica gel
$SOCl_2$ Thionyl Chloride
T3P® Propylphosphonic acid anhydride
TBAF Tetrabutylammonium fluoride
TBDMS t-Butyldimethylsilyl
TBTU O-(Benzotriazol-1-yl)-N,N,N',N'-tetramethyluronium tetrafluoroborate
TEA Triethylamine
TFA Trifluoroacetic acid
THF Tetrahydrofuran
TLC Thin Layer Chromatography
TsCl toluene sulfonyl chloride
TsOH toluene sulfonic acid Compounds of the present invention are prepared from commonly available compounds using procedures known to those skilled in the art in view of the examples and schemes provided herein.

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005, 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der Organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethyl hexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent sometimes being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralization of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallization and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Intermediates and final products can be worked up and/or purified according to standard methods, e.g., using chromatographic methods, distribution methods, (re-) crystallization, and the like.

EXAMPLES

The invention is further illustrated by the following examples, which should not be construed as limiting. The assays used throughout the Examples are well established in the art: demonstration of efficacy in these assays is generally regarded as predictive of efficacy in subjects.

The compounds of the invention can be produced by organic synthesis methods known to one of ordinary skill in the art with reference to the following reaction schemes and examples. General methods for synthesis of compounds of Formula (I) are provided in Schemes below.

High Resolution Mass Spectrometry by LC-MS

ESI-MS data were recorded using a LTQ-XL Orbitrap mass spectrometer (ThermoFisher Scientific) with electrospray ionization source. The resolution of the MS system was approximately 30000. The drug candidate was infused into the mass spectrometer by UPLC (Acquity, Waters) from sample probe. The separation was performed on Acquity UPLC BEH C18 1×50 mm column at 0.15 mL/min flow rate with the gradient from 5% to 95% in 3 min. Solvent A was Water with 0.1% Trifluoroacetic acid and solvent B was 75% Methanol and 25% Isopropyl alcohol with 0.1% Trifluoroacetic acid. The mass accuracy of the system has been found to be <5 ppm.

Examples 1 and 2: N-((4bR,9bR)-1-amino-4b-hydroxy-7-isopropyl-10-oxo-4b,10-dihydro-9bH-indeno[1,2-b]benzofuran-9b-yl)acetamide

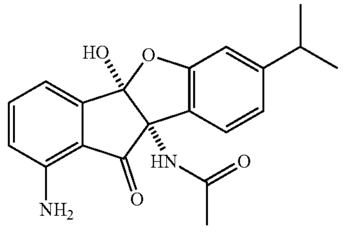

12

+

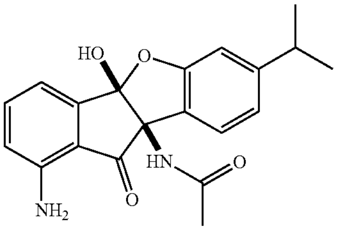

13

Scheme 1

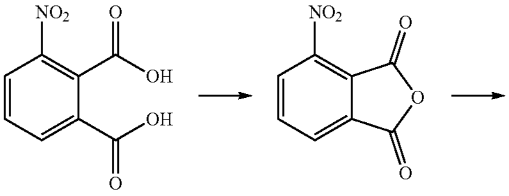

1

2

-continued

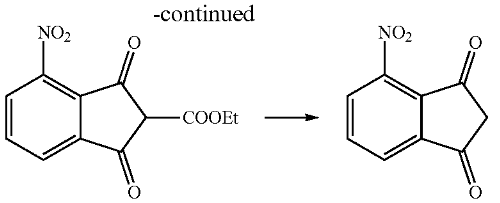

3

4

4-Nitroisobenzofuran-1,3-dione (2)

An initial suspension of the 3-nitrophthalic acid 1 (1.0 kg, 4.7 moles) in $Ac_2O$ (1 Ltr), was refluxed at 140° C. for 2.5 hours. This was then cooled down to 80° C. and added slowly to diethyl ether (4 Ltr) with vigorous stirring. The precipitate was collected by filtration over Buckner funnel and this was washed with $Et_2O$ to give the product as a solid.

Ethyl 4-nitro-1,3-dioxo-2,3-dihydro-1H-indene-2-carboxylate (3)

To a suspension of the anhydride 2 (50 g, 0.26 moles) in dry DCM (260 mL), ethyl acetoacetate (42 mL, 0.31 moles) and $Ac_2O$ (48.5 mL, 0.52 moles) were added at ambient temperature. To this suspension $Et_3N$ (108 mL, 0.78 moles) was charged at room temperature dropwise in a duration of 30 minutes. This was stirred at the same temperature for 15 mins more and then DCM was evaporated off. The crude obtained was then dissolved in 2 liters of water and cooled to 0° C. This was fixed with an overhead stirrer and under vigorous stirring conditions 300 mL of 2 N HCl was added to it dropwise maintaining the temperature below 0° C. This was stirred at 0° C. for more 15 mins and then filtered over Buckner funnel and washed with ice cold water (500 mL). This was then air dried for three days to get the product.

4-Nitro-1H-indene-1,3(2H)-dione (4)

Ethyl 4-nitro-1,3-dioxo-2,3-dihydro-1H-indene-2-carboxylate 3 (272.5 g, 1.04 moles) was taken in 1 liter of MeCN:water (20:1, 1.0 M). This suspension was charged with TFA (60 mL, 1.14 moles) slowly at room temperature and then kept for heating at 50° C. After 4 hrs, the reaction mass was concentrated over rotavapour until approximately 100 mL of solvent remains. The precipitated solid was then filtered off over Buckner funnel and washed with (1:1) $CHCl_3$:Hexane. This gives a solid product and the filtrate was again concentrated to get more product in second crop.

Scheme 2

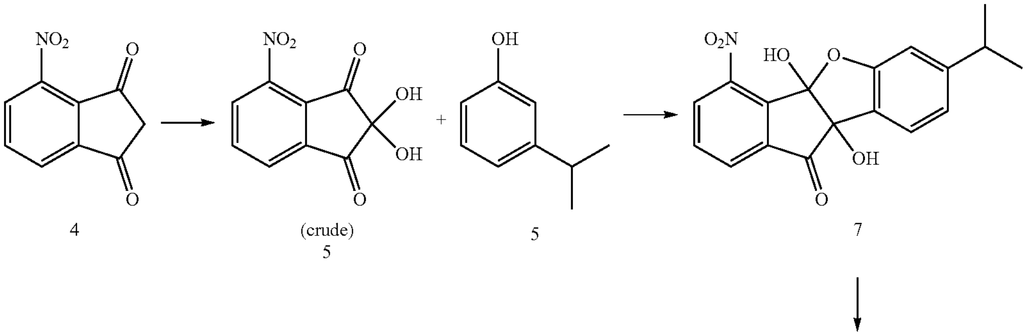

4

(crude)
5

5

7

-continued

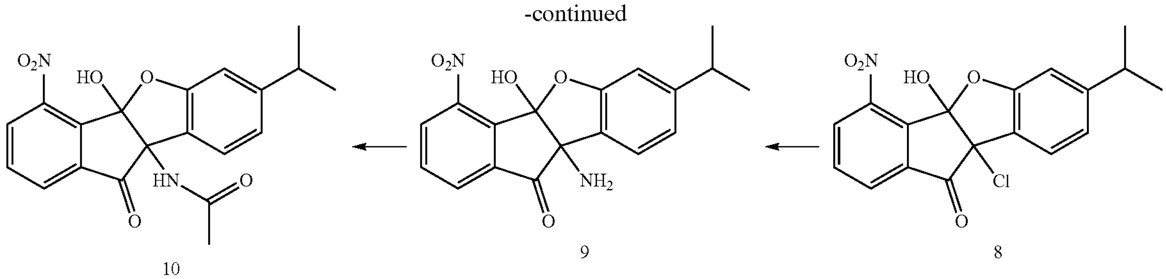

10 9 8

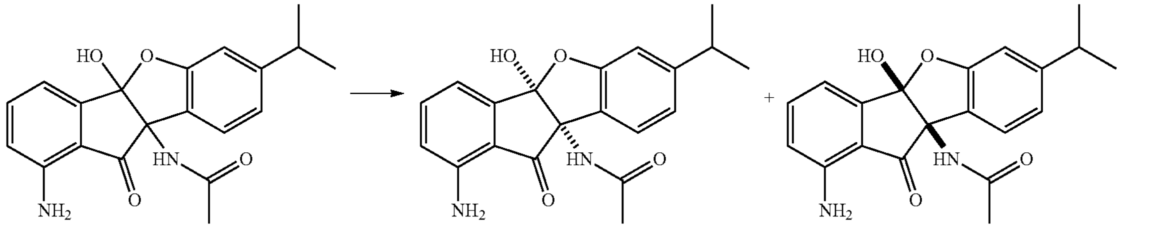

11 12 13

2,2-Dihydroxy-4-nitro-JH-indene-1,3(2H)-dione (S)

4-Nitro-1H-indene-1,3(2H)-dione (4) (250 g, 1.31 moles) was taken in 1,4-dioxane (2 liter) and AcOH (200 ml). To this $SeO_2$ (291 g, 2.62 moles) was added at room temperature and kept for reflux at 110° C. for next 4 hours. This was stirred at room temperature for next 12 hours. This was then charged with 500 g-600 g of CELITE. This was stirred nicely and filtered over CELITE pad. The residue was washed with ethyl acetate (300-500 mL). The filtrate obtained was concentrated to get the crude mass which was then used as such in next step.

4b,9b-Dihydroxy-7-isopropyl-4-nitro-4b,9b-dihydro-10H-indeno[1,2-b]benzofuran-10-one (7)

2,2-Dihydroxy-4-nitro-1H-indene-1,3(2H)-dione 5 (crude, 1.31 moles) was taken in glacial AcOH (2 liter) and charged with 3-isopropyl phenol 6 (196 g, 1.44 moles) and kept for reflux for next 10 hours. This was then concentrated completely and purified over silica gel column chromatography (30% EA in hexanes) to get the pure product.

9b-Chloro-4b-hydroxy-7-isopropyl-4-nitro-4b,9b-dihydro-10H-indeno[1,2-b]benzofuran-10-one (8)

4b,9b-Dihydroxy-7-isopropyl-4-nitro-4b,9b-dihydro-10H-indeno[1,2-b]benzofuran-10-one 7 (50 g, 0.147 moles) was taken in DCM (500 mL) and this suspension was then charged with oxalyl chloride (1.2 eq) in a single lot. This was then slowly charged with DMF (50 mL). The reaction mass was then left to stir at room temperature for next 6 hours. This was quenched with water (500 mL) and the layers were separated. The aqueous layer was extracted with DCM (300 mL×2). The combined organic layer was washed with water (300 mL) and brine (300 mL). This was dried over sodium sulfate and concentrated to get the crude mass which was then purified over short pad of silica (30% ethylacetate in hexanes) to get the pure product. mp: $^1$H-NMR (300 MHz, $CDCl_3$): δ 1.18 (dd, J=3.6 Hz, J=6.9 Hz, 6H), 2.84 (sept, J=6.9 Hz, 1H), 6.34 (s, 1H), 6.70 (s, 1H), 6.94 (dd, J=1.0 Hz, J=7.8 Hz, 1H), 7.45 (d, J=7.8 Hz, 1H), 7.81-7.83 (m, 1H), 8.21 (m, 1H), 8.52 (m, 1H).

9b-Amino-4b-hydroxy-7-isopropyl-4-nitro-4b,9b-dihydro-10H-indeno[1,2-b]benzofuran-10-one (9)

9b-Chloro-4b-hydroxy-7-isopropyl-4-nitro-4b,9b-dihydro-10H-indeno[1,2-b]benzofuran-10-one 8 (36.0 g, 0.1 mole) was taken in THF (350 mL) and cooled to −40° C. To this 2.0 M solution of $NH_3$ in IPA (100 mL, 0.20 moles) was added using a dropping funnel and temperature was maintained below −20° C. The reaction mass was monitored at −20° C. for an hour and then allowed to warm to room temperature. This was stirred at room temperature until the completion of the reaction and then concentrated completely. The crude was taken in ethylacetate (500 mL) and washed with water (200 mL×2) and brine (100 mL). This was dried over anhy. $Na_2SO_4$ and then concentrated to get the crude mass which was purified over short pad of silica to get the pure product. $^1$H-NMR (300 MHz, $CDCl_3$) δ 1.18 (d, J=6.9 Hz, 6H), 2.84 (sept, J=6.9 Hz, 1H), 3.46 (s, 1H), 6.25 (s, 1H), 6.74 (s, 2H), 6.90 (dd, J=1.2 Hz, J=7.8 Hz, 1H), 7.55 (d, J=7.8 Hz, 1H), 7.77 (t, J=8.1 Hz, 1H), 8.22 (dd, J=1.2 Hz, J=8.4 Hz, 1H), 8.52 (dd, J=1.2 Hz, J=8.1 Hz, 1H).

N-(4b-hydroxy-7-isopropyl-4-nitro-10-oxo-4b,10-dihydro-9bH-indeno[1,2-b]benzofuran-9b-yl)acetamide (10)

9b-amino-7-cyclopropyl-4b-hydroxy-4-nitro-4b,9b-dihydro-10H-indeno[1,2-b]benzofuran-10-one 9 (950 mg, 2.80 mmol) was taken in AcOH (10 mL, 0.1 M) and to this acetic anhydride (0.263 mL, 2.8 mmol) was added at ambient temperature. This was heated at 80° C. for next 30 minutes. The reaction mass was concentrated off and then taken in EA (100 mL). This was washed with water (30 mL) and brine (30 mL). This was dried over anhy. $Na_2SO_4$ and concentrated. The crude obtained was purified over silica gel column chromatography (30-40% EA in hexanes) to get the pure product.

N-(1-amino-4b-hydroxy-7-isopropyl-10-oxo-4b,10-dihydro-9bH-indeno[1,2-b]benzofuran-9b-yl)acetamide (11)

N-(4b-hydroxy-7-isopropyl-4-nitro-10-oxo-4b,10-dihydro-9bH-indeno[1,2-b]benzofuran-9b-yl)acetamide 10 (500 mg, 1.3 mmol) was taken in EtOH:water (10:1, 15 mL, 0.1 M) and to this Fe powder (0.219 mg, 3.92 mmol) was added. This was charged with catalytic amount of conc. HCl (3 drops) and allowed to reflux at 90° C. for next 3 hours. The reaction mass was filtered over CELITE under hot conditions and EA was used to wash the residues. This was concentrated off and then taken in EA (250 mL). This was washed with water (100 mL) and brine (100 mL). This was dried over anhy. $Na_2SO_4$ and concentrated. The crude obtained was purified over silica gel column chromatography (1:1=EA:hexanes) to get the pure product.

N-((4bR,9bR)-1-amino-4b-hydroxy-7-isopropyl-10-oxo-4b,10-dihydro-9bH-indeno[1,2-b]benzofuran-9b-yl)acetamide (12) and N-((4bS,9bS)-1-amino-4b-hydroxy-7-isopropyl-10-oxo-4b,10-dihydro-9bH-indeno[1,2-b]benzofuran-9b-yl)acetamide (13)

N-(1-amino-4b-hydroxy-7-isopropyl-10-oxo-4b,10-dihydro-9bH-indeno[1,2-b]benzofuran-9b-yl)acetamide (560 mg) was purified by chiral chromatography using (AD column, SFC=100 ml/min, CO2/EtOH=70/30, 236 bar) to give 243 mg of N-((4bR,9bR)-1-amino-4b-hydroxy-7-isopropyl-10-oxo-4b,10-dihydro-9bH-indeno[1,2-b]benzofuran-9b-yl)acetamide 12 as (peak 2, tR 4.33 min.); 1H NMR (500 MHz, METHANOL-d4) δ 7.41-7.50 (m, 1H), 7.32-7.40 (m, 1H), 6.94-7.03 (m, 1H), 6.79-6.91 (m, 1H), 6.58-6.74 (m, 2H), 2.77-2.94 (m, 1H), 1.96-2.05 (m, 3H), 1.12-1.26 (m, 6H) and 246 mg of N-((4bS,9bS)-1-amino-4b-hydroxy-7-isopropyl-10-oxo-4b,10-dihydro-9bH-indeno[1,2-b]benzofuran-9b-yl)acetamide 13 as (peak 1, tR 2.30 min.); 1H NMR (400 MHz, METHANOL-d4) δ: 7.39-7.46 (m, 1H), 7.35 (br d, J=7.8 Hz, 1H), 6.97 (br d, J=7.3 Hz, 1H), 6.84 (br d, J=7.6 Hz, 1H), 6.61-6.69 (m, 2H), 2.82 (dt, J=13.6, 6.8 Hz, 1H), 1.98 (s, 3H), 1.17 (dd, J=6.9, 1.6 Hz, 6H).

Examples 3-5: N-(1-amino-4b-hydroxy-10-oxo-7-(trifluoromethyl)-4b,10-dihydro-9bH-indeno[1,2-b]benzofuran-9b-yl)acetamide (19); N-((4bR,9bR)-1-amino-4b-hydroxy-10-oxo-7-(trifluoromethyl)-4b,10-dihydro-9bH-indeno[1,2-b]benzofuran-9b-yl)acetamide (20) and N-((4bS,9bS)-1-amino-4b-hydroxy-10-oxo-7-(trifluoromethyl)-4b,10-dihydro-9bH-indeno[1,2-b]benzofuran-9b-yl)acetamide (21)

19

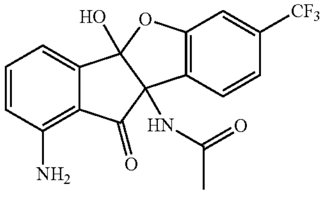

-continued

20

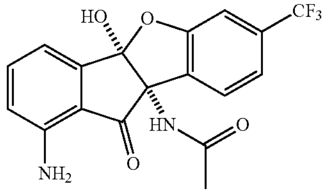

21

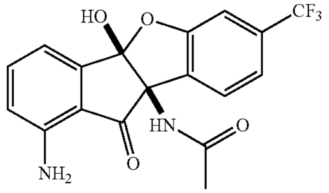

N-(1-amino-4b-hydroxy-10-oxo-7-(trifluoromethyl)-4b,10-dihydro-9bH-indeno[1,2-b]benzofuran-9b-yl)acetamide (19) (500 mg) was purified by chiral chromatography using (AD column, SFC=100 ml/min, CO2/IPA=80/20, 226 bar) to give N-((4bR,9bR)-1-amino-4b-hydroxy-10-oxo-7-(trifluoromethyl)-4b,10-dihydro-9bH-indeno[1,2-b]benzofuran-9b-yl)acetamide (20) as (peak 2, tR 4.50 min.); 1H NMR (500 MHz, METHANOL-d4) δ 7.58-7.70 (m, 1H), 7.42-7.53 (m, 1H), 7.26 (br d, J=7.80 Hz, 1H), 6.97-7.11 (m, 2H), 6.67-6.83 (m, 1H), 2.02 (s, 3H) and N-((4bS,9bS)-1-amino-4b-hydroxy-10-oxo-7-(trifluoromethyl)-4b,10-dihydro-9bH-indeno[1,2-b]benzofuran-9b-yl)acetamide (21) as (peak 1, tR 2.49 min.); 1H NMR (500 MHz, METHANOL-d4) δ: −1.13 (br d, J=7.6 Hz, 1H), −1.29 (br t, J=7.6 Hz, 1H), −1.50 (br d, J=7.3 Hz, 1H), −1.79-−1.69 (m, 2H), −2.09-−1.95 (m, 1H), −6.75 (s, 3H).

Scheme 3

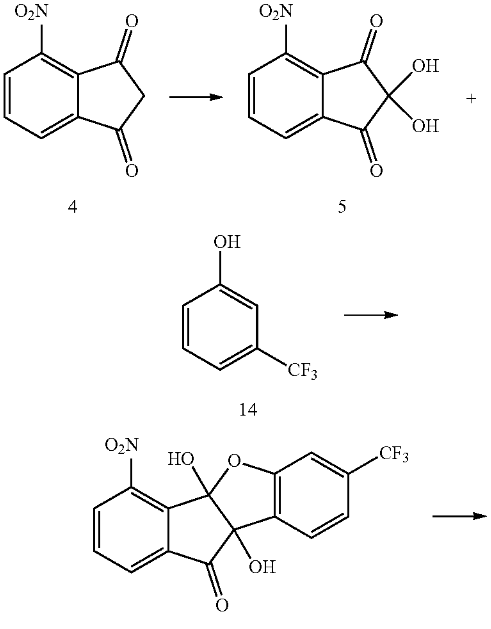

4

5

14

15

-continued

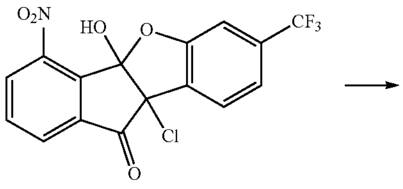

16

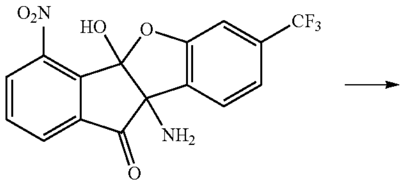

17

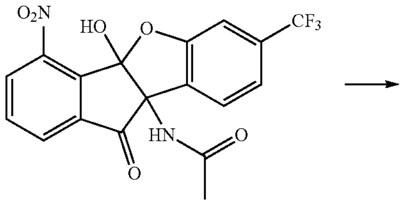

18

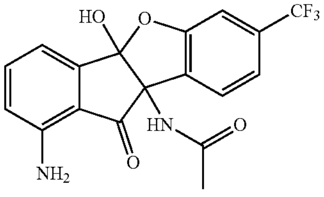

19

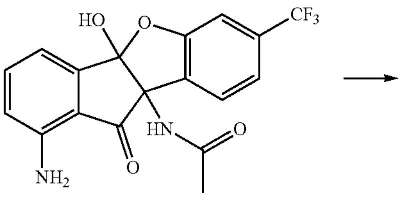

19

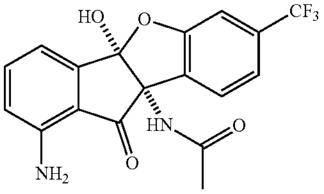

+

20

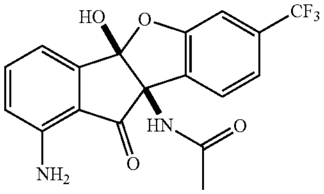

21

4b,9b-Dihydroxy-4-nitro-7-(trifluoromethyl)-4b,9b-dihydro-10H-indeno[1,2-b]benzofuran-10-one (15)

To a solution of 4-nitro-1H-indene-1,3(2H)-dione 4 (42.1 g, 0.22 mol) in 1,4 dioxane:AcOH (10:1, 330 mL, 0.6 M) was added $SeO_2$ (48.8 g, 0.44 mol). The resulting solution was refluxed at 130° C. for 3 hours. This was then cooled down and filtered over CELITE using EA (~200 mL). The filtrate was concentrated off completely and crude 2,2-Dihydroxy-4-nitro-1H-indene-1,3(2H)-dione 5 was taken in $MeSO_3H$ (350 mL, 0.6 M). To this 3-(trifluoromethyl) phenol 14 (29 mL, 0.24 mol) was added dropwise and left to stir at room temperature (30° C.) for next 24 h. The reaction mass was then quenched in ice water (1500 mL) and the solid was filtered off. The residue was dissolved in EA (500 mL) and washed with water (200 ml) and brine (200 mL). This was dried over anhy. $Na_2SO_4$ and concentrated to crude. Crude was purified over silica gel column chromatography (10-40% EA in hexanes with 5-10% DCM) to get the pure product.

9b-Chloro-4b-hydroxy-4-nitro-7-(trifluoromethyl)-4b,9b-dihydro-10H-indeno[1,2-b]benzofuran-10-one (16)

4b,9b-Dihydroxy-4-nitro-7-(trifluoromethyl)-4b,9b-dihydro-10H-indeno[1,2-b]benzofuran-10-one 15 (25 g, 68 mmol) was taken in DCM (270 mL, 0.25 M) and charged with oxalyl chloride (7.1 mL, 82 mmol) at room temperature. To this DMF (26 mL, 340 mmol) was added slowly and left to stir at ambient temperature (20° C.). The reaction mixture was then stirred at room temperature (20° C.) for next 6 hours. The reaction was again charged with oxalyl chloride (1.8 mL, 0.3 eq) and left to stir for next 12 hours. The reaction mixture was diluted with water (~300 mL). The aq. layer was extracted with DCM (~300 mL×2). The combined org. layers were washed with water (~300 ml) and brine (~300 mL). This was dried over anhy. $Na_2SO_4$ and concentrated off to get the crude product. Crude was purified over silica gel column chromatography (10-25% EA in hexane) to get the pure product.

9b-Amino-4b-hydroxy-4-nitro-7-(trifluoromethyl)-4b,9b-dihydro-10H-indeno[1,2-b]benzofuran-10-one (17)

9b-Chloro-4b-hydroxy-4-nitro-7-(trifluoromethyl)-4b,9b-dihydro-10H-indeno[1,2-b]benzofuran-10-one 16 (20.5 g, 53 mmol) was taken in THF (350 mL, 0.15 M) and cooled to −40° C. To this 2.0 M $NH_3$ in IPA (65 mL, 0.13 mol) was added dropwise in a duration of 10 min. The reaction mixture was then left to stir at −40° C. for next 3 hours. This was then diluted with EA (~200-300 mL) and washed with 10% brine (~200 mL×2). The organic layer was dried over anhy. $Na_2SO_4$ and concentrated off to get the crude product.

N-(4b-hydroxy-4-nitro-10-oxo-7-(trifluoromethyl)-4b,10-dihydro-9bH-indeno[1,2-b]benzofuran-9b-yl) acetamide (18)

9b-Amino-4b-hydroxy-4-nitro-7-(trifluoromethyl)-4b,9b-dihydro-10H-indeno[1,2-b]benzofuran-10-one 17 (21 g, 50 mmol) was taken in gl. AcOH (250 mL, 0.2 M) and immediately charged with $Ac_2O$ (9.5 mL, 0.1 mol). The reaction mixture was then heated at 80° C. for next 60 mins. The reaction mixture was concentrated off to get the crude. The crude mass was directly purified over silica gel column chromatography (20-40% EA in Hx with 10% DCM as cosolvent) to get the pure product.

N-(1-amino-4b-hydroxy-10-oxo-7-(trifluoromethyl)-4b,10-dihydro-9bH-indeno[1,2-b]benzofuran-9b-yl) acetamide (19)

N-(4b-hydroxy-4-nitro-10-oxo-7-(trifluoromethyl)-4b,10-dihydro-9bH-indeno[1,2-b]benzofuran-9b-yl)acetamide 18 (9.0 g, 22 mmol) was taken in EtOH:water (10:1, 110 mL, 0.2 M), and to this Fe powder (3.7 g, 66 mmol) was charged followed by conc. HCl (0.5 mL). This was refluxed at 90° C. for next 3 hours. The reaction mass was filtered over CELITE under warm conditions using hot EA (~50-100 mL). The filtrate was concentrated off & taken in EA (~600-800 mL) and washed with water (400 mL). The aq. layer was extracted with EA (~200 mL×2). The combined organic layers was the washed with water (~300 mL) and brine (~200 mL). This was dried over anhy. $Na_2SO_4$ and concentrated off to (~100-150 mL). The solid precipitated was then sonicated well and filtered off to get the pure product. The filtrate was concentrated off to get the crude. Crude was purified over silica gel column chromatography (20-50% EA in Hx with DCM as additive) to get additional amount of pure product. $^1$H-NMR (300 MHz, $CD_3OD$) δ 2.0 (s, 3H), 6.74 (s, 1H), 7.00-7.02 (m, 2H), 7.24 (d, J=7.8 Hz, 1H), 7.43-7.48 (m, 1H), 7.61 (d, J=7.8 Hz, 1H). LCMS: 378.6 $[M+H]^+$.

| Molecular Formula | Isotopic Mass | calculated mass for $MH^+$ | measured mass for $MH^+$ | LCMS [M + H]+ | UV RT (min) |
|---|---|---|---|---|---|
| $C_{18}H_{13}F_3N_2O_4$ | 378.0827 | 379.09 | 379.0901 | 379.0 | 2.2 |

N-((4bR,9bR)-1-amino-4b-hydroxy-10-oxo-7-(trifluoromethyl)-4b,10-dihydro-9bH-indeno[1,2-b]benzofuran-9b-yl)acetamide (20)

N-(1-amino-4b-hydroxy-10-oxo-7-(trifluoromethyl)-4b,10-dihydro-9bH-indeno[1,2-b]benzofuran-9b-yl)acetamide (19) (500 mg) was purified by chiral chromatography using (AD column, SFC=100 ml/min, CO2/IPA=80/20, 226 bar) to give 202 mg of N-((4bR,9bR)-1-amino-4b-hydroxy-10-oxo-7-(trifluoromethyl)-4b,10-dihydro-9bH-indeno[1,2-b]benzofuran-9b-yl)acetamide (20) as (peak 2, tR 4.50 min.); 1H NMR (500 MHz, METHANOL-d4) δ 7.58-7.70 (m, 1H), 7.42-7.53 (m, 1H), 7.26 (br d, J=7.80 Hz, 1H), 6.97-7.11 (m, 2H), 6.67-6.83 (m, 1H), 2.02 (s, 3H) and 205 mg of N-((4bS,9bS)-1-amino-4b-hydroxy-10-oxo-7-(trifluoromethyl)-4b,10-dihydro-9bH-indeno[1,2-b]benzofuran-9b-yl)acetamide (21) as (peak 1, tR 2.49 min.); 1H NMR (500 MHz, METHANOL-d4) δ: −1.13 (br d, J=7.6 Hz, 1H), −1.29 (br t, J=7.6 Hz, 1H), −1.50 (br d, J=7.3 Hz, 1H), −1.79--1.69 (m, 2H), −2.09--1.95 (m, 1H), −6.75 (s, 3H).

Example 6: N-((4bR,9bR)-1-amino-7-bromo-4b-hydroxy-10-oxo-4b,10-dihydro-9bH-indeno[1,2-b]benzofuran-9b-yl)acetamide (31)

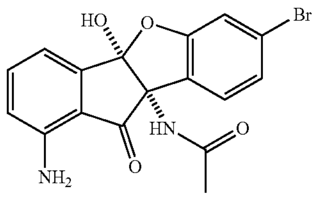

Scheme 4

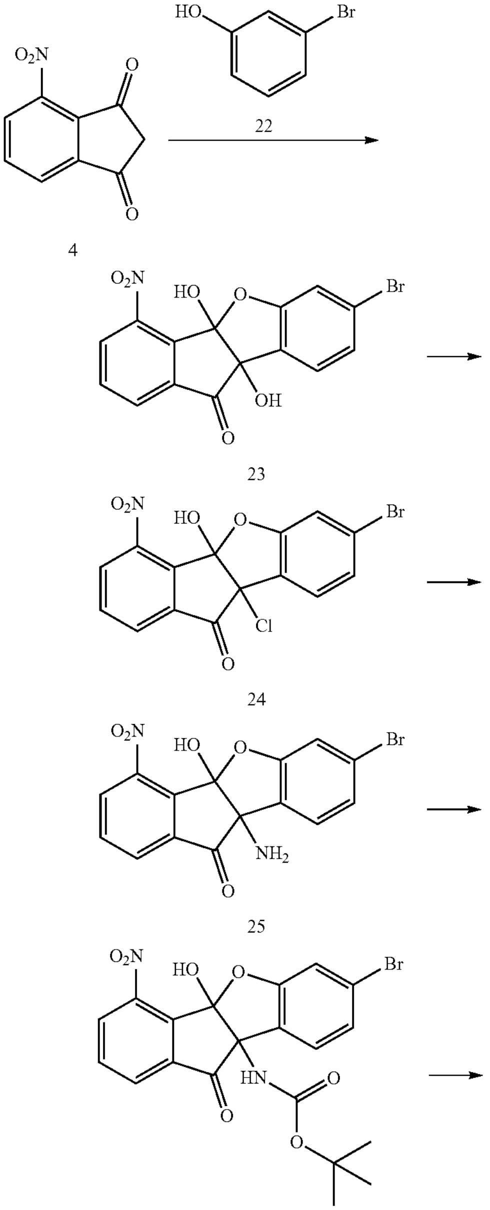

4
22
23
24
25
26

-continued

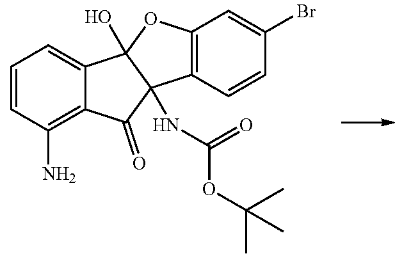

27

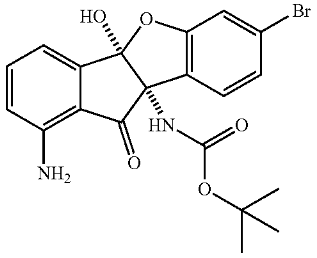

28

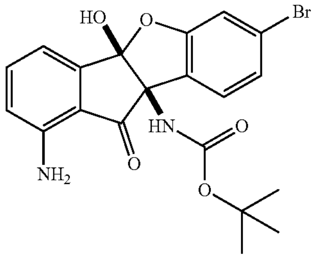

29

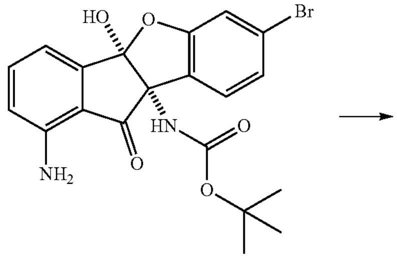

28

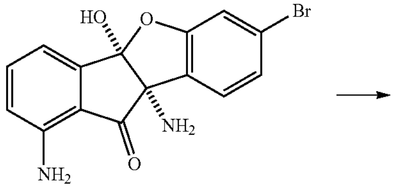

30

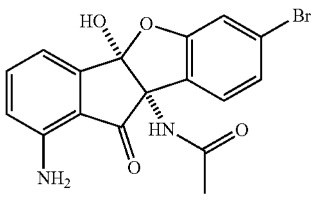 [SMILES: CC(=O)N[C@]12C(=O)c3c(N)cccc3[C@@]1(O)Oc1cc(Br)ccc12]

31

7-Bromo-4b,9b-dihydroxy-4-nitro-4b,9b-dihydro-10H-indeno[1,2-b]benzofuran-10-one (23)

4-Nitro-1H-indene-1,3(2H)-dione 4 (10.0 g, 52.3 mmol) was taken in AcOH:dioxane (1:10, 105 mL, 0.5 M). This was charged with $SeO_2$ (12.77 g, 115.1 mmol) and refluxed for 5 hours at 105-110° C. The reaction mass was then filtered over CELITE under hot conditions and then concentrated off the volatiles to get the crude 2,2-Dihydroxy-4-nitro-1H-indene-1,3(2H)-dione 5. This crude product was then taken in gl. AcOH (210 mL, 0.25 mmol) and this was charged with 3-bromo phenol 22 (9.96 g, 57.5 mmol) and kept at reflux for next 12 hours. The reaction mass was concentrated off and taken in EA (500-600 mL). This was filtered over CELITE and residue washed with EA. The filtrate was washed with water (200 mL×2) and brine (100 mL). This was dried over anhyd. $Na_2SO_4$ and concentrated off to get the crude product. The crude was purified over silica gel column chromatography (35-40% EA in hexanes) twice to get the pure product.

7-Bromo-9b-chloro-4b-hydroxy-4-nitro-4b,9b-dihydro-10H-indeno[1,2-b]benzofuran-10-one (24)

7-bromo-4b,9b-dihydroxy-4-nitro-4b,9b-dihydro-10H-indeno[1,2-b]benzofuran-10-one 23 (39.5 g, 0.105 mol) was taken in DCM (520 mL, 0.2 M) and charged with oxalyl chloride (11 mL, 0.13 mol) at room temperature. To this DMF (40 mL, 0.53 mol) was added slowly (0.05 mL/min over 30 mins, then 0.1 mL/min over 30 min, then the remainder) and left to stir at ambient temperature (30° C.). The reaction mixture was then stirred at rt (20° C.) for next 12 hours. The reaction mixture was diluted with water (~300 mL). The aq. layer was extracted with DCM (~500 mL×2). The combined org. layer was washed with water (~300 ml) and brine (~300 mL). This was dried over anhy. $Na_2SO_4$ and concentrated off to get the crude product. Crude was purified over silica gel column chromatography (10-30% EA in hexane) to get the pure product.

9b-Amino-7-bromo-4b-hydroxy-4-nitro-4b,9b-dihydro-10H-indeno[1,2-b]benzofuran-10-one (25)

9b-Chloro-4b-hydroxy-4-nitro-8-(trifluoromethyl)-4b,9b-dihydro-10H-indeno[1,2-b]benzofuran-10-one 24 (21.2 g, 53.4 mmol) was taken in THF (530 mL, 0.1 M) and cooled to −40° C. This was charged with 2.0 M $NH_3$ in IPA (54 mL, 0.11 mmol) at same temperature and left to stir for next 3 h. The reaction mixture was diluted with water (~150 mL) and brine (150 mL). The aq. layer was extracted with EA (~300 mL×2). The combined org. layer was washed with brine (~100 mL). This was dried over anhy. $Na_2SO_4$ and concentrated off to get the crude product. Crude was purified over silica gel column chromatography (20-30% EA in hexanes with 20% DCM as cosolvent) to get the pure product.

Tert-butyl (7-bromo-4b-hydroxy-4-nitro-10-oxo-4b,10-dihydro-9bH-indeno[1,2-b]benzofuran-9b-yl) carbamate (26)

Boc anhydride (8.74 g, 40 mmol) and Molecular 12 (0.69 g, 2.67 mmol) was added to a solution of a racemic mixture of 9b-amino-7-bromo-4b-hydroxy-4-nitro-4b,9b-dihydro-10H-indeno[1,2-b]benzofuran-10-one 25 (10.1 g, 31 mmol) in THF (5.0 mL, 5.0 M) and stirred at rt (30° C.) for next 72 h. The reaction mass was concentrated off and purified. The crude was purified over silica gel column chromatography (10%-30% EA in hexanes with 5-10% DCM) to get the pure product.

Tert-butyl (1-amino-7-bromo-4b-hydroxy-10-oxo-4b,10-dihydro-9bH-indeno[1,2-b]benzofuran-9b-yl) carbamate (27)

A mixture racemic tert-butyl (7-bromo-4b-hydroxy-4-nitro-10-oxo-4b,10-dihydro-9bH-indeno[1,2-b]benzofuran-9b-yl)carbamate 26 (10.3 g, 21.5 mmol) was taken in EtOH:water (10:1, 110.0 mL, 0.20 M), and to this Fe powder (3.57 g, 63.9 mmol) was charged followed by Conc. HCl (0.8 mL, cat.). This was refluxed at 90° C. for next 3 hours. The reaction mass was filtered over CELITE under warm conditions using hot EA (50-100 mL). The filtrate was concentrated off & taken in EA (~1000-1200 mL) and washed with water (~300-500 mL) and brine (~300 mL). This was dried over anhy. $Na_2SO_4$ and concentrated to get the crude. Crude was purified over silica gel column chromatography (10-30% EA in hx) to get the pure product.

Tert-butyl ((4bR,9bR)-1-amino-7-bromo-4b-hydroxy-10-oxo-4b,10-dihydro-9bH-indeno[1,2-b]benzofuran-9b-yl)carbamate (28) and tert-butyl ((4bR,9bR)-1-amino-7-bromo-4b-hydroxy-10-oxo-4b,10-dihydro-9bH-indeno[1,2-b]benzofuran-9b-yl) carbamate (29)

Tert-butyl (1-amino-7-bromo-4b-hydroxy-10-oxo-4b,10-dihydro-9bH-indeno[1,2-b]benzofuran-9b-yl)carbamate (27) was purified by chiral chromatography using (AD column, HPLC=20 ml/min, Heptane/EtOH=70/30, 724 psi) to give tert-butyl ((4bR,9bR)-1-amino-7-bromo-4b-hydroxy-10-oxo-4b,10-dihydro-9bH-indeno[1,2-b]benzofuran-9b-yl)carbamate (28) as (peak 2, tR 15.59 min.); 1H NMR (500 MHz, METHANOL-d4) δ: 7.48 (br t, J=7.7 Hz, 1H), 7.37 (br s, 1H), 7.11 (br s, 1H), 7.02 (br d, J=7.1 Hz, 1H), 6.95 (s, 1H), 6.72 (br s, 1H), 1.42 (br s, 5H), 1.13 (br s, 4H) LCMS: 447.2/449.2 $[M+H]^+$ and tert-butyl ((4bS,9bS)-1-amino-7-bromo-4b-hydroxy-10-oxo-9b,10-dihydro-4bH-indeno[1,2-b]benzofuran-9b-yl)carbamate (29) as (peak 1, tR 8.97 min.); 1H NMR (500 MHz, METHANOL-d4) δ: 7.48 (br t, J=7.6 Hz, 1H), 7.37 (br s, 1H), 7.11 (br s, 1H), 7.02 (br d, J=6.9 Hz, 1H), 6.95 (s, 1H), 6.72 (br s, 1H), 1.42 (br s, 5H), 1.13 (br s, 4H) LCMS: 447.2/449.2 $[M+H]^+$ (4bR,9bR)-1,9b-Diamino-7-bromo-4b-hydroxy-4b,9b-dihydro-10H-indeno[1,2-b]benzofuran-10-one (30)

Tert-butyl ((4bR,9bR)-1-amino-7-bromo-4b-hydroxy-10-oxo-4b,10-dihydro-9bH-indeno[1,2-b]benzofuran-9b-yl) carbamate 28 (112 mg, 0.25 mmol) was taken in DCM (2.5 mL, 0.1 M) and immediately charged with 4.0 M HCl in dioxane (0.63 mL, 2.50 mmol). The reaction mixture was then stirred at r.t. (20° C.) for next 6 hours. The reaction mixture was diluted with EA (50 mL) and stirred with sat. $NaHCO_3$(20 mL) for 5-10 mins vigorously. The layers were separated off and aq. layer was extracted with EA (30 mL×2). The combined org. layer was washed with water (20 ml) and brine (20 mL). This was dried over anhy. $Na_2SO_4$ and concentrated off to get the product. Crude was used as such in next step without further purifications.

N-((4bR,9bR)-1-amino-7-bromo-4b-hydroxy-10-oxo-4b,10-dihydro-9bH-indeno[1,2-b]benzofuran-9b-yl)acetamide (31)

(4bR,9bR)-1,9b-Diamino-7-bromo-4b-hydroxy-4b,9b-dihydro-10H-indeno[1,2-b]benzofuran-10-one 30 (76 mg, 0.22 mmol) was taken in gl. AcOH (2.2 mL, 0.1 M) and immediately charged with $Ac_2O$ (0.03 mL, 1.2 mmol). The reaction mixture was then heated at 80° C. for next 30 mins. Then 10 mL of 2 N HCl (aq.) was added and stirred for next 2 hours at 80° C. The reaction mixture was concentrated off to get the crude. The crude mass was directly purified over silica gel column chromatography (20-50% EA in Hx with 1-2% MeOH as cosolvent) to get the pure product as. $^1$H-NMR (300 MHz, MeOD) δ 7.50-7.40 (br, 1H), 7.40-7.25 (br, 1H), 7.10 (d, J=7.4 Hz, 1H), 7.05-6.85 (m, 2H), 6.69 (br, 1H), 1.99 (s, 3H).

| Molecular Formula | Isotopic Mass | calculated mass for $MH^+$ | measured mass for $MH^+$ | LCMS [M + H]+ | UV RT (min) |
|---|---|---|---|---|---|
| $C_{17}H_{13}BrN_2O_4$ | 388.0059 | 389.0132 | 389.0130 | 389.1 | 2.08 |

Examples 7-9: N-(1-amino-7-cyclopropyl-4b-hydroxy-10-oxo-4b,10-dihydro-9bH-indeno[1,2-b]benzofuran-9b-yl)acetamide (40); N-((4bR,9bR)-1-amino-7-cyclopropyl-4b-hydroxy-10-oxo-4b,10-dihydro-9bH-indeno[1,2-b]benzofuran-9b-yl) acetamide (41) and N-((4bS,9bS)-1-amino-7-cyclopropyl-4b-hydroxy-10-oxo-4b,10-dihydro-9bH-indeno[1,2-b]benzofuran-9b-yl)acetamide (42)

40

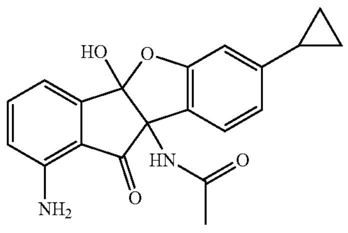

41

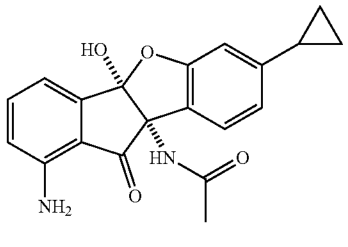

42

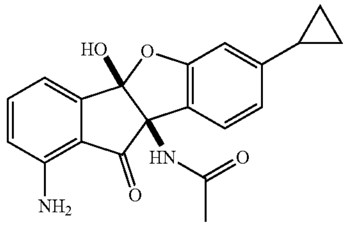

Scheme 5

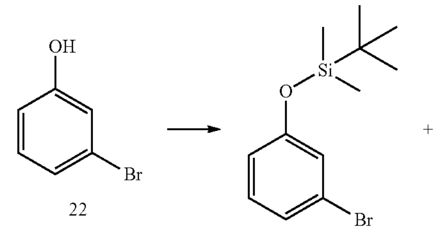

22 32

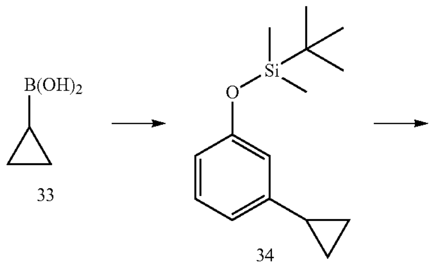

33 34

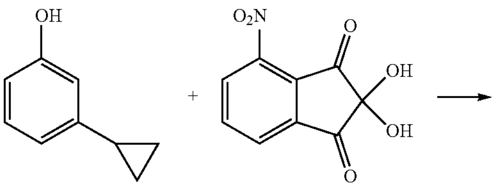

35 5

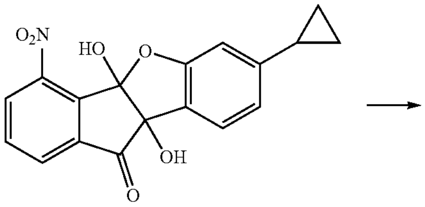

36

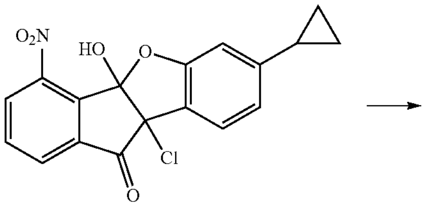

37

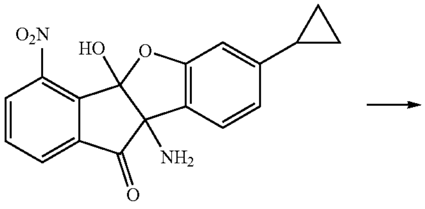

38

-continued

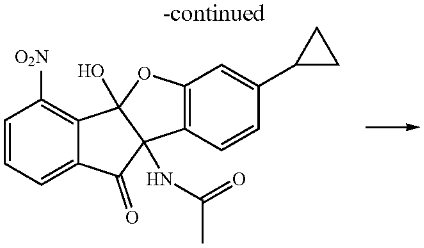

39

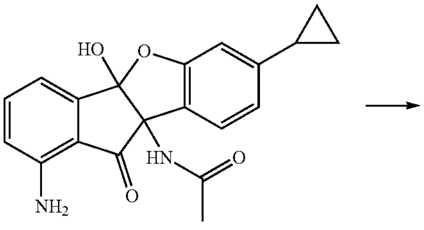

40

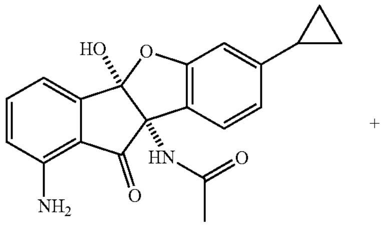

41

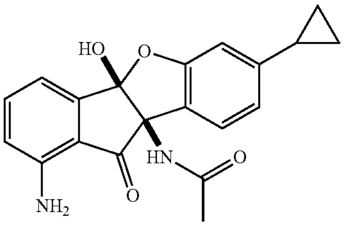

42

(3-Bromophenoxy)(tert-butyl)dimethylsilane (32)

3-Bromophenol 22 (2.08 g, 12 mmol) was taken in dry DCM (40 mL, 0.3 M). This was charged with TBDMS-Cl (2.0 g, 13 mmol). This was then charged with imidazole (1.37 g, 20 mmol) and allowed to stir at room temperature for next 15 hours. The reaction mass was directly filtered off and residue washed with DCM. The filtrate was concentrated and crude obtained was purified over silica gel column chromatography (0-5% EA:hexanes) to get the pure product. $^{1}$H-NMR (300 MHz, $CDCl_3$) δ 0.20 (s, 6H), 0.97 (s, 9H), 6.74-6.78 (m, 1H), 7.00 (s, 1H), 7.07-7.09 (m, 1H).

Tert-butyl(3-cyclopropylphenoxy)dimethylsilane (34)

(3-Bromophenoxyxtert-butyl)dimethylsilane 32 (430 mg, 1.5 mmol) was taken in toluene:water (previously purged with nitrogen) (7.33 mL, 0.2 M). This was charged with cyclopropane boronic acid 33 (154 mg, 1.8 mmol). This was then charged with $PCy_3$ (42 mg, 0.15 mmol), $K_3PO_4$ (1.1 g, 5.24 mmol) and $Pd(OAc)_2$ (17 mg, 0.07 mmol). This was then allowed to reflux at 110° C. for next 3 hour. The reaction mass was passed through CELITE and washed with ether. The organic layer was washed with water (30 mL) and brine (30 mL). This was dried over anhyd. $Na_2SO_4$ and concentrated to get the crude which was purified over silica gel column chromatography (0-5% EA:hexanes) to get the pure product. $^1$H-NMR (300 MHz, $CDCl_3$) δ 0.19 (s, 6H), 0.63-0.68 (m, 2H), 0.89-1.02 (m, 11H), 1.79-1.88 (m, 1H), 6.52-6.54 (m, 1H), 6.59-6.68 (m, 2H), 7.06-7.11 (m, 1H).

3-Cyclopropylphenol (35)

Tert-butyl(3-cyclopropylphenoxy)dimethylsilane 34 (1.74 g, 7.0 mmol) was taken in THF (23 mL, 0.3 M) and to this 1.0 M TBAF (9.1 mL, 9.1 mmol) was added. This was stirred at room temperature for next 75 mins. The reaction mass was concentrated and then taken in EA (200 mL). This was washed with sat. $NH_4Cl$ (50 mL), water (50 mL) and brine (50 mL). This was dried over anhyd. $Na_2SO_4$ and concentrated. The crude obtained was purified over silica gel column chromatography (5% EA in hexanes) to get the pure product. $^1$H-NMR (500 MHz, $CDCl_3$) δ 0.69-0.73 (m, 2H), 0.95-0.99 (m, 2H), 1.85-1.90 (m, 1H), 4.71 (br, 1H), 6.56-6.57 (m, 1H), 6.63 (dd, J=2.5 Hz, J=8.0 Hz, 1H), 6.70 (d, J=8.0 Hz, 1H), 7.13-7.16 (m, 1H, ArH).

7-Cyclopropyl-4b,9b-dihydroxy-4-nitro-4b,9b-dihydro-10H-indeno[1,2-b]benzofuran-10-one (36)

2,2-dihydroxy-4-nitro-1H-indene-1,3(2H)-dione 5 (1.80 g, 8.0 mmol) and 3-cyclopropylphenol 35 (1.1 g, 8.0 mmol) was refluxed in gl. AcOH (40 mL, 0.2 M) for 2 hours. The reaction mass was concentrated off and dissolved in EA (200 mL). This was washed with water (50 mL) and brine (50 mL). This was dried over anhy. $Na_2SO_4$ and concentrated off. The crude obtained was then taken in DCM:hexanes (50 mL appx) and the solid obtained was sonicated. This was filtered off to get the pure product. The filtrate was concentrated again and purified over silica gel column chromatography (30% EA in hexanes) to get the remaining product. $^1$H-NMR (300 MHz, $CD_3OD$) δ 0.65-0.67 (m, 2H), 0.95-0.99 (m, 2H), 1.81-1.86 (m, 1H), 3.67 (br, 1H), 6.22 (br, 1H), 6.50 (s, 1H), 6.77 (d, J=8.0 Hz, 1H), 7.43 (d, J=8.0 Hz, 1H), 7.78-7.82 (m, 1H), 8.18 (d, J=7.5 Hz, 1H), 8.50 (d, J=8.0 Hz, 1H).

9b-Chloro-7-cyclopropyl-4b-hydroxy-4-nitro-4b,9b-dihydro-10H-indeno[1,2-b]benzofuran-10-one (37)

7-cyclopropyl-4b,9b-dihydroxy-4-nitro-4b,9b-dihydro-10H-indeno[1,2-b]benzofuran-10-one 36 (1.70 g, 5.0 mmol) was taken in DCM (20 mL, 0.25 M) and charged with oxalyl chloride (0.52 mL, 6.0 mmol). This was then charged slowly with DMF (2 mL). After 3 hours additional oxalyl chloride (0.08 mL) was added. The reaction was then stirred at room temperature for next 30 min. The reaction mass was diluted with DCM to 200 mL. This was washed with water (100 mL×2). This was then washed with saturated brine (100 mL) and dried over anhy. $Na_2SO_4$. This was concentrated off to get the crude which was purified over silica gel column chromatography (10-15% EA in Hx) to get the pure product. $^1$H-NMR (300 MHz, $CDCl_3$) δ 0.61-0.68 (m, 2H), 0.93-0.99 (m, 2H), 1.81-1.87 (m, 1H), 6.28 (br, 1H), 6.49 (s, 1H), 6.78 (d, J=8.1 Hz, 1H, ArH), 7.39 (d, J=8.1 Hz, 1H), 7.78-7.823 (m, 1H), 8.19 (d, J=7.5 Hz, 1H), 8.49 (d, J=8.1 Hz, 1H).

9b-Amino-7-cyclopropyl-4b-hydroxy-4-nitro-4b,9b-dihydro-10H-indeno[1,2-b]benzofuran-10-one (38)

9b-chloro-7-cyclopropyl-4b-hydroxy-4-nitro-4b,9b-dihydro-10H-indeno[1,2-b]benzofuran-10-one 37 (715 mg, 2.0 mmol) was taken in dry THF (20.0 mL, 0.1 M). This was cooled to −40° C. and then charged with 2.0 M $NH_3$ in IPA (2.0 mL, 4.0 mmol). This was then stirred at −40° C. to −30° C. for next 2 hour. The reaction mass was concentrated off to half the volume at 25° C. and then quenched with water. This was again concentrated to remove all the volatiles and then taken in EA (150 mL). This was washed with water (50 mL×2) and brine (50 mL). This was dried over anhyd. $Na_2SO_4$ and concentrated. The crude obtained was purified over silica gel column chromatography previously deactivated with TEA (1:2=EA:hexanes) to get the pure product. $^1$H-NMR (300 MHz, $CD_3OD$) δ 0.59-0.64 (m, 2H), 0.85-0.90 (m, 2H), 1.73-1.85 (m, 1H), 6.56 (s, 1H), 6.81 (d, J=7.8 Hz, 1H), 7.46 (d, J=7.8 Hz, 1H), 7.77-7.80 (m, 1H), 8.25 (d, J=7.5 Hz, 1H), 8.58 (d, J=8.1 Hz, 1H).

9b-Chloro-7-cyclopropyl-4b-hydroxy-4-nitro-4b,9b-dihydro-10H-indeno[1,2-b]benzofuran-10-one (39)

2,4,6 trichlorobenzoic acid (168 mg, 0.75 mmol) was taken in THF (5 mL, 0.1 M) and to this NMM (0.083 mL, 0.75 mmol) was added at 0° C. This was charged with acetyl chloride (0.054 mL, 0.75 mmol) and allowed to stir at 0° C. for next 30 minutes. This was then charged with 9b-amino-7-cyclopropyl-4b-hydroxy-4-nitro-4b,9b-dihydro-10H-indeno[1,2-b]benzofuran-10-one 38 (170 mg, 0.5 mmol) in a single lot and stirred at 0° C. for next 3 hours. The reaction mass was concentrated off and then taken in EA (100 mL). This was washed with water (30 mL) and brine (30 mL). This was dried over anhy. $Na_2SO_4$ and concentrated. The crude obtained was purified over silica gel column chromatography (1:1=EA:hexanes) to get the pure product. $^1$H-NMR (300 MHz, $CDCl_3$) δ 0.59-0.64 (m, 2H), 0.92-0.98 (m, 2H), 1.77-1.85 (m, 1H), 2.07 (s, 3H), 6.06 (br, 1H), 6.46 (br, 2H), 6.76 (dd, J=7.8 Hz, J=1.2 Hz, 1H), 7.38 (d, J=7.8 Hz, 1H), 7.71-7.76 (m, 1H), 8.19 (d, J=7.5 Hz, 1H), 8.45 (d, J=7.8 Hz, 1H).

N-(1-amino-7-cyclopropyl-4b-hydroxy-10-oxo-4b,10-dihydro-9bH-indeno[1,2-b]benzofuran-9b-yl)acetamide (40)

N-(7-cyclopropyl-4b-hydroxy-4-nitro-10-oxo-4b,10-dihydro-9bH-indeno[1,2-b]benzofuran-9b-yl)acetamide 39 (150 mg, 0.39 mmol) was taken in EtOH:water (10:1, 8 mL, 0.05 M) and to this Fe powder (66 mg, 1.18 mmol) was added. This was charged with 2 drops of conc. HCl and then reaction was refluxed for next 2 hours. The reaction mass was filtered over CELITE and the residue was washed with EA in hot conditions. The filtrate was concentrated off and the crude was taken in EA (100 mL). This was washed with water (30 mL) and brine (30 mL). This was dried over anhy. $Na_2SO_4$ and concentrated off. The crude obtained was then purified over silica gel column chromatography (1:1=EA in hexanes) to get the pure product. $^1$H-NMR (300 MHz, $CD_3OD$) δ 0.59-0.61 (m, 2H), 0.89-0.92 (m, 2H), 1.79-1.85 (m, 1H), 2.01 (s, 3H), 6.44 (s, 1H), 6.52-6.72 (m, 2H), 6.95-7.02 (m, 1H), 7.29-7.32 (m, 1H), 7.39-7.44 (m, 1H).

| Molecular Formula | Isotopic Mass | calculated mass for $MH^+$ | measured mass for $MH^+$ | LCMS [M + H]+ | UV RT (min) |
|---|---|---|---|---|---|
| $C_{20}H_{18}N_2O_4$ | 350.1267 | 351.134 | 351.1338 | 351.2 | 2.04 |

N-((4bR,9bR)-1-amino-7-cyclopropyl-4b-hydroxy-10-oxo-4b,10-dihydro-9bH-indeno[1,2-b]benzofuran-9b-yl)acetamide (41) and N-((4bS,9bS)-1-amino-7-cyclopropyl-4b-hydroxy-10-oxo-4b,10-dihydro-9bH-indeno[1,2-b]benzofuran-9b-yl) acetamide (42)

N-(1-amino-7-cyclopropyl-4b-hydroxy-10-oxo-4b,10-dihydro-9bH-indeno[1,2-b]benzofuran-9b-yl)acetamide (40) (500 mg) was purified by chiral chromatography using (AD column, HPLC=20 ml/min, Heptane/EtOH=70/30, 722 psi) to give N-((4bR,9bR)-1-amino-7-cyclopropyl-4b-hydroxy-10-oxo-4b,10-dihydro-9bH-indeno[1,2-b]benzofuran-9b-yl) acetamide (41) as (peak 2, tR 17.95 min.); 1H NMR (500 MHz, METHANOL-d4) δ: 7.43 (br s, 1H), 7.30 (br s, 1H), 6.98 (br s, 1H), 6.60-6.76 (m, 2H), 6.45 (br s, 1H), 1.99 (s, 3H), 1.84 (br s, 1H), 0.91 (br d, J=8.0 Hz, 2H), 0.58-0.66 (m, 2H).

| Molecular Formula | Isotopic Mass | calculated mass for $MH^+$ | measured mass for $MH^+$ | LCMS [M + H]+ | UV RT (min) |
|---|---|---|---|---|---|
| $C_{20}H_{18}N_2O_4$ | 350.1267 | 351.134 | 351.1342 | 351.1 | 2.04 |

and N-((4bS,9bS)-1-amino-7-cyclopropyl-4b-hydroxy-10-oxo-4b,10-dihydro-9bH-indeno[1,2-b]benzofuran-9b-yl) acetamide (42) as (peak 1, tR 9.16 min.); 1H NMR (500 MHz, METHANOL-d4) δ: 7.44 (br d, J=2.8 Hz, 1H), 7.33 (br d, J=5.7 Hz, 1H), 7.00 (br d, J=1.7 Hz, 1H), 6.73 (br d, J=6.9 Hz, 1H), 6.64-6.71 (m, 1H), 6.47 (br s, 1H), 2.00 (s, 3H), 1.79-1.92 (m, 1H), 0.86-0.99 (m, 2H), 0.57-0.70 (m, 2H).

| Molecular Formula | Isotopic Mass | calculated mass for $MH^+$ | measured mass for $MH^+$ | LCMS [M + H]+ | UV RT (min) |
|---|---|---|---|---|---|
| $C_{20}H_{18}N_2O_4$ | 350.1267 | 351.134 | 351.1337 | 351.1 | 2.04 |

Examples 10-12: N-(1-amino-4b-hydroxy-10-oxo-7-(trifluoromethoxy)-4b,10-dihydro-9bH-indeno[1,2-b]benzofuran-9b-yl)acetamide (48); N-((4bR,9bR)-1-amino-4b-hydroxy-10-oxo-7-(trifluoromethoxy)-4b,10-dihydro-9bH-indeno[1,2-b]benzofuran-9b-yl) acetamide (49) and N-((4bS,9bS)-1-amino-4b-hydroxy-10-oxo-7-(trifluoromethoxy)-4b,10-dihydro-9bH-indeno[1,2-b]benzofuran-9b-yl) acetamide (50)

48

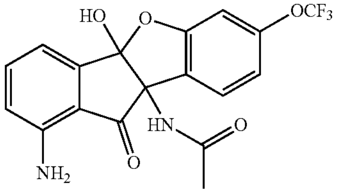

-continued

49

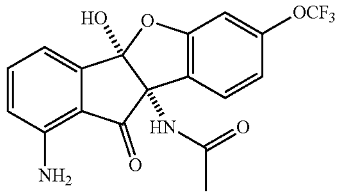

50

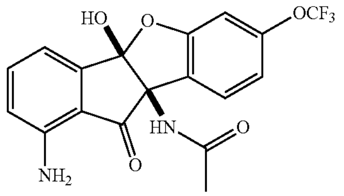

Scheme 6

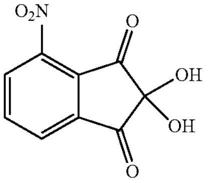

5

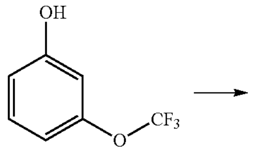

43

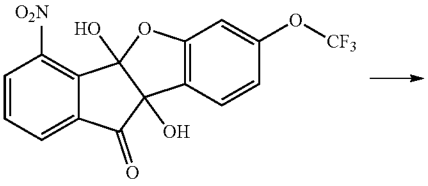

44

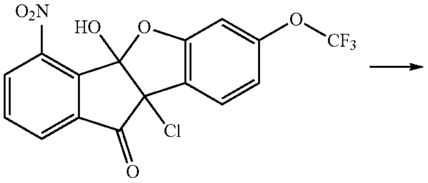

45

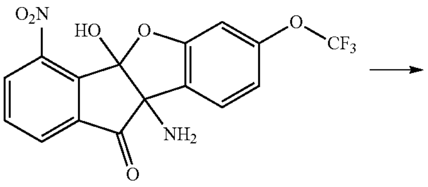

46

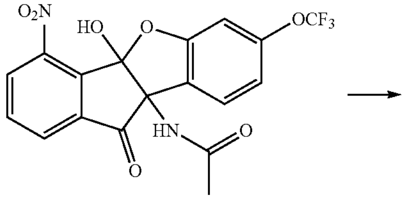

47

-continued

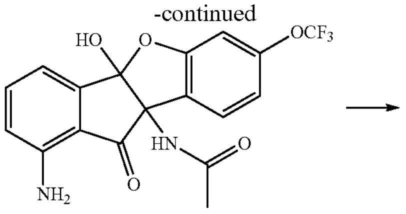

48

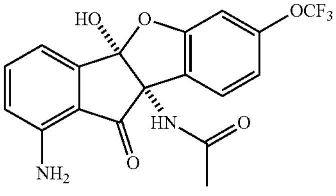

49

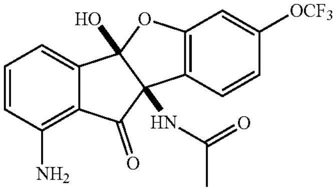

50

4b, 9b-Dihydroxy-4-nitro-7-(trifluoromethoxy)-4b, 9b-dihydro-10H-indeno[1,2-b]benzofuran-10-one (44)

2,2-Dihydroxy-4-nitro-1H-indene-1,3(2H)-dione 5 (1.34 g, 6 mmol) was taken in TFA (24 mL, 0.25 M). To this 3-(trifluoromethoxy)phenol 43 (1.07 g, 6 mmol) was charged and this was stirred at room temperature (30° C.) for next 12 hours. The reaction mass was concentrated off. This was then taken in EA (200 mL) and washed with water (100 mL×2) and brine (100 mL). This was dried over anhyd. $Na_2SO_4$ and concentrated to get the crude mass. The crude product was then purified over silica gel column chromatography (1:2=EA in hexanes) to get the pure product.

9b-Chloro-4b-hydroxy-4-nitro-7-(trifluoromethoxy)-4b,9b-dihydro-10H-indeno[1,2-b]benzofuran-10-one (45)

4b,9b-Dihydroxy-4-nitro-7-(trifluoromethoxy)-4b,9b-dihydro-10H-indeno[1,2-b]benzofuran-10-one 44 (385 mg, 1.0 mmol) was taken in DCM (4.0 mL, 0.25 M). To this oxalyl chloride (0.103 mL, 1.21 mmol) was charged followed by DMF (0.4 mL, 5.0 mmol) and stirred at room temperature (30° C.) for 3 hours. The reaction mass was diluted with DCM (~100 mL) and washed with water (50 mL×2) and brine (50 mL), dried over anhyd. $Na_2SO_4$ and concentrated off to get the crude. The crude was purified over silica gel column chromatography (10-15% EA in hexanes) to get the pure product.

9b-Amino-4b-hydroxy-4-nitro-7-(trifluoromethoxy)-4b,9b-dihydro-JOH-indeno[1,2-b]benzofuran-10-one (46)

9b-Chloro-4b-hydroxy-4-nitro-7-(trifluoromethoxy)-4b, 9b-dihydro-10H-indeno[1,2-b]benzofuran-10-one 45 (200 mg, 0.50 mmol) was taken in THF (5.0 mL, 0.1 M). This was cooled to −40° C. and charged with 2.0 M $NH_3$ in IPA (0.5 mL, 1.0 mmol) and allowed to warm at −10° C. in next 3 hours. The reaction mass was concentrated off and quenched with water (50 mL) and extracted with EA (100 mL). The combined organic layers were washed with water (50 mL) and brine (30 mL), dried over anhyd. $Na_2SO_4$ and concentrated off to get the crude. The crude was purified over short pad of silica gel column chromatography (30-40% EA in hexanes) to get the pure product.

N-(4b-Hydroxy-4-nitro-10-oxo-7-(trifluoromethoxy)-4b,10-dihydro-9bH-indeno[1,2-b]benzofuran-9b-yl)acetamide (47)

2,4,6 Trichlorobenzoic acid (89 mg, 0.40 mmol) was taken in THF (2.0 mL, 0.1 M) and this was cooled to 0° C. To this NMM (0.44 mL, 0.40 mmol) was added followed by AcCl (0.021 mL, 0.30 mmol). The reaction mass was stirred at for 10 mins and to this 9b-amino-4b-hydroxy-4-nitro-7-(trifluoromethoxy)-4b,9b-dihydro-10H-indeno[1,2-b]benzofuran-10-one 46 (76 mg, 0.2 mmol) was added. The reaction mass was stirred at 0° C. for next 1.5 hours. The reaction mass was concentrated off and the residue was quenched with water (50 mL) and extracted with EA (50 mL×2). The combined organic layer was washed with water (30 mL) and brine (30 mL), dried over anhyd. $Na_2SO_4$ and concentrated off to get the crude. The crude product was purified over silica gel column chromatography (30-35% EA in hexanes) to get the pure product.

N-(1-Amino-4b-hydroxy-10-oxo-7-(trifluoromethoxy)-4b,10-dihydro-9bH-indeno[1,2-b]benzofuran-9b-yl)acetamide (48)

N-(4b-hydroxy-4-nitro-10-oxo-7-(trifluoromethoxy)-4b, 10-dihydro-9bH-indeno[1,2-b]benzofuran-9b-yl)acetamide 47 (21 mg, 0.05 mmol) was taken in EtOH:water (10:1, 2.5 mL, 0.02 M) and charged with Fe powder (8.3 mg, 0.15 mmol). This was charged with conc. HCl (1 drop) and refluxed at 90° C. for next 3 hours. The reaction mass was filtered over CELITE under hot conditions. The residue was washed with EA (~20 mL). This was concentrated off and then taken in EA (~50 mL). This was washed with water (~20 mL) and brine (~20 mL). This was dried over anhyd. $Na_2SO_4$ and concentrated to get the crude mass. The crude mass was directly purified over reverse phase HPLC (MeCN:water as eluent) to get the pure product. $^1$H-NMR (300 MHz, $CD_3OD$) δ 2.01 (s, 3H), 6.71 (s, 1H), 6.77 (d, J=8.4 Hz, 1H), 6.87 (d, J=8.4 Hz, 1H), 7.02 (d, J=7.2 Hz, 1H), 7.45-7.52 (m, 2H).

| Molecular Formula | Isotopic Mass | calculated mass for $MH^+$ | measured mass for $MH^+$ | LCMS [M + H]+ | UV RT (min) |
|---|---|---|---|---|---|
| $C_{18}H_{13}F_3N_2O_5$ | 394.0777 | 395.085 | 395.0847 | 395.1 | 2.27 |

N-((4bR,9bR)-1-amino-4b-hydroxy-10-oxo-7-(trifluoromethoxy)-4b,10-dihydro-9bH-indeno[1,2-b]benzofuran-9b-yl)acetamide (49) and N-((4bS,9bS)-1-amino-4b-hydroxy-10-oxo-7-(trifluoromethoxy)-4b,10-dihydro-9bH-indeno[1,2-b]benzofuran-9b-yl)acetamide (50)

N-(1-Amino-4b-hydroxy-10-oxo-7-(trifluoromethoxy)-4b,10-dihydro-9bH-indeno[1,2-b]benzofuran-9b-yl)acetamide (48) (200 mg) was purified by chiral chromatography using (AD column, SFC=100 ml/min, CO2/IPA=85/15, 206 bar) to give N-((4bR,9bR)-1-amino-4b-hydroxy-10-oxo-7-(trifluoromethoxy)-4b,10-dihydro-9bH-indeno[1,2-b]benzofuran-9b-yl)acetamide (49) as (peak 2, tR 7.41 min.); 1H NMR (500 MHz, METHANOL-d4) δ: 7.37-7.55 (m, 2H), 7.00 (d, J=7.3 Hz, 1H), 6.85 (br d, J=8.3 Hz, 1H), 6.75 (br d, J=6.9 Hz, 1H), 6.69 (s, 1H), 1.99 (s, 3H).

| Molecular Formula | Isotopic Mass | calculated mass for $MH^+$ | measured mass for $MH^+$ | LCMS [M + H]+ | UV RT (min) |
|---|---|---|---|---|---|
| $C_{18}H_{13}F_3N_2O_5$ | 394.0777 | 395.085 | 395.0846 | 395.1 | 2.27 |

and N-((4bS,9bS)-1-amino-4b-hydroxy-10-oxo-7-(trifluoromethoxy)-4b,10-dihydro-9bH-indeno[1,2-b]benzofuran-9b-yl)acetamide (50) as (peak 1, tR 4.10 min.); 1H NMR (500 MHz, METHANOL-d4) δ: 7.42-7.52 (m, 2H), 7.00 (d, J=7.3 Hz, 1H), 6.84 (br d, J=8.3 Hz, 1H), 6.75 (br d, J=8.3 Hz, 1H), 6.68 (s, 1H), 1.99 (s, 3H).

| Molecular Formula | Isotopic Mass | calculated mass for $MH^+$ | measured mass for $MH^+$ | LCMS [M + H]+ | UV RT (min) |
|---|---|---|---|---|---|
| $C_{18}H_{13}F_3N_2O_5$ | 394.0777 | 395.085 | 395.0846 | 395.1 | 2.27 |

Examples 13-15: N-(1-amino-7-chloro-4b-hydroxy-10-oxo-4b,10-dihydro-9bH-indeno[1,2-b]benzofuran-9b-yl)acetamide and N-((4bR,9bR)-1-amino-7-chloro-4b-hydroxy-10-oxo-4b,10-dihydro-9bH-indeno[1,2-b]benzofuran-9b-yl)acetamide and N-((4bS,9bS)-1-amino-7-chloro-4b-hydroxy-10-oxo-4b,10-dihydro-9bH-indeno[1,2-b]benzofuran-9b-yl)acetamide

56

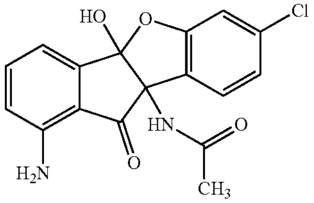

57

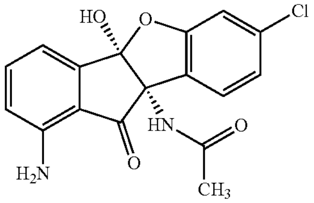

58

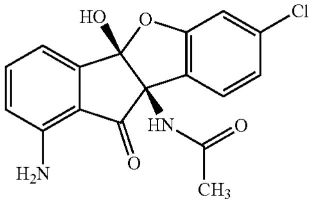

Scheme 7

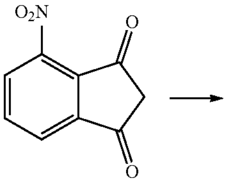

4

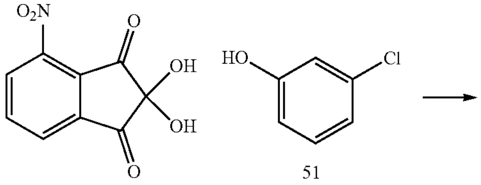

5

51

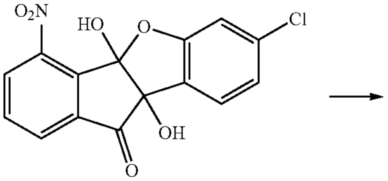

52

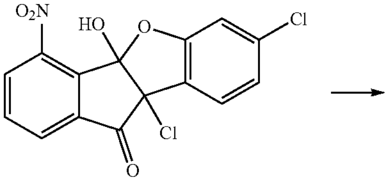

53

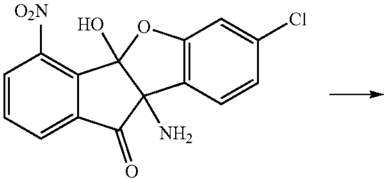

54

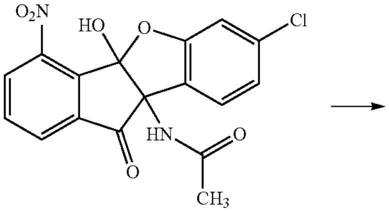

55

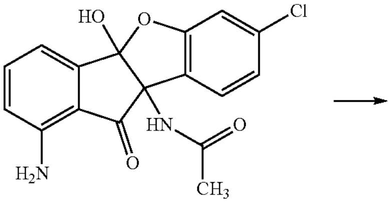

56

-continued

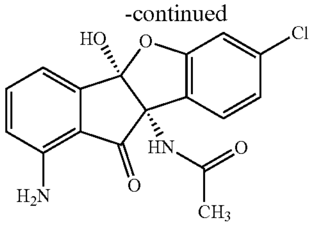

+

57

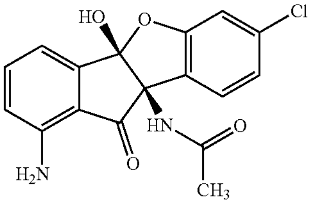

58

2,2-Dihydroxy-4-nitro-1H-indene-1,3(2H)-dione (5)

To the mixture of 4-nitro-1H-indene-1,3(2H)-dione 4 (2.3 g, 12 mmol) in Dioxane:AcoH (20 mL/2 mL) was added selenium dioxide (2.7 g, 24 mmol). The resulting reaction mass was refluxed at 130° C. for 3 h. The reaction mass was cooled to ambient temperature and diluted with ethyl acetate and filtered through CELITE bed and was washed with ethyl acetate evaporated solvent to get crude. The residue was used for next step as such without purification.

7-Chloro-4b,9b-dihydroxy-4-nitro-4b,9b-dihydro-10H-indeno[1,2-b]benzofuran-10-one (52)

To the mixture of 2,2-dihydroxy-4-nitro-1H-indene-1,3 (2H)-dione 5 (3.7 g, crude) in Acetic acid (20 mL) was added 3-Chlorophenol 51 (1.6 g, 12 mmol). The resulting reaction mass was refluxed at 110° C. for 12 h The reaction mass was cooled to ambient temperature and diluted with ethyl acetate and filtered through CELITE bed and was washed with ethyl acetate evaporated solvent to get crude. Crude was purified over silica-gel column chromatography (ethyl acetate:hexane) to get the product.

7,9b-Dichloro-4b-hydroxy-4-nitro-4b,9b-dihydro-10H-indeno[1,2-b]benzofuran-10-one (53)

To the mixture of 7-chloro-4b,9b-dihydroxy-4-nitro-4b, 9b-dihydro-10H-indeno[1,2-b]benzofuran-10-one 52 (400 mg, 1.2 mmol) in DCM (6 mL) was added Oxalyl chloride (0.12 mL, 1.44 mmol), to the resulting reaction mass was added DMF (0.4 mL) dropwise for 1 h, then reaction mass was stirred at ambient temperature for 15 h. The reaction mass was diluted with DCM and washed with water (50 mL×2) the organic layer was then washed with brine solution, dried over $Na_2SO_4$ and the solvent was evaporated to get crude. Crude was purified over silica-gel column chromatography (ethyl acetate:hexane) to get the product.

9b-Amino-7-chloro-4b-hydroxy-4-nitro-4b,9b-dihydro-10H-indeno[1,2-b]benzofuran-10-one (54)

To the mixture of 7,9b-dichloro-4b-hydroxy-4-nitro-4b, 9b-dihydro-10H-indeno[1,2-b]benzofuran-10-one 53 (220 mg, 0.63 mmol) in THF (3 mL) at −40° C. was added Ammonia in IPA (0.8 mL, 1.6 mmol) for 5 min, the reaction mass was stirred at −40° C. for 2 h. The reaction mass was diluted with ethyl acetate and washed with brine solution (50 mL×2). The organic layer was then dried over $Na_2SO_4$ and solvent evaporated to get (crude) product. Crude was used as such for next step without purification N-(7-Chloro-4b-hydroxy-4-nitro-10-oxo-4b,10-dihydro-9bH-indeno[1,2-b]benzofuran-9b-yl)acetamide (55)

To the solution of 9b-amino-7-chloro-4b-hydroxy-4-nitro-4b,9b-dihydro-10H-indeno[1,2-b]benzofuran-10-one 54 (210 mg, 0.63 mmol) in AcoH (6 mL) Acetic anhydride (0.07 mL, 0.76 mmol) was added. The resulting reaction mass was stirred at 80° C. for 1 h. The reaction mass evaporated to dryness and the residue was dissolved in ethyl acetate (50 mL) organic layer was washed with water (25 mL×2) organic layer was dried over $Na_2SO_4$ and evaporated solvent to get crude. Crude was purified over silica-gel column chromatography (ethyl acetate:hexane) to get the product.

N-(1-Amino-7-chloro-4b-hydroxy-10-oxo-4b,10-dihydro-9bH-indeno[1,2-b]benzofuran-9b-yl)acetamide (56)

To the solution of N-(7-chloro-4b-hydroxy-4-nitro-10-oxo-4b,10-dihydro-9bH-indeno[1,2-b]benzofuran-9b-yl)acetamide (100 mg, 0.26 mmol) in EtOH:$H_2O$ (9 mL) Fe powder (45 mg 0.8 mmol) and Conc HCl (1 drop) were added. The resulting reaction mass was stirred at 90° C. for 3 h. The reaction mass was filtered through CELITE bed and was washed with ethyl acetate. The solvent was evaporated to get a residue and the residue was dissolved in ethyl acetate (100 mL). Organic layer was washed with water (50 mL×2), dried over $Na_2SO_4$, and solvent evaporated to get crude. Crude was purified over silica-gel column chromatography using (ethyl acetate:hexane) to get the product. $^1H$ NMR (300 MHz, Methanol-$d_4$) δ 7.62-7.24 (m, 2H), 6.99 (t, J=8.8 Hz, 2H), 6.82 (d, J=1.9 Hz, 1H), 6.72 (s, 1H), 2.01 (s, 3H).

| Molecular Formula | Isotopic Mass | calculated mass for $MH^+$ | measured mass for $MH^+$ | LCMS [M + H]+ | UV RT (min) |
|---|---|---|---|---|---|
| $C_{17}H_{13}ClN_2O_4$ | 344.0564 | 345.0637 | 345.0636 | 345.0 | 2.02 |

N-((4bR,9bR)-1-amino-7-chloro-4b-hydroxy-10-oxo-4b,10-dihydro-9bH-indeno[1,2-b]benzofuran-9b-yl)acetamide (57) and N-((4bS,9bS)-1-amino-7-chloro-4b-hydroxy-10-oxo-4b,10-dihydro-9bH-indeno[1,2-b]benzofuran-9b-yl)acetamide (58)

N-(1-Amino-7-chloro-4b-hydroxy-10-oxo-4b,10-dihydro-9bH-indeno[1,2-b]benzofuran-9b-yl)acetamide (56) (200 mg) was purified by chiral chromatography using (IC column, SFC=100 ml/min, CO2/MeOH=85/15, 206 bar) to give N-((4bR,9bR)-1-amino-7-chloro-4b-hydroxy-10-oxo-4b,10-dihydro-9bH-indeno[1,2-b]benzofuran-9b-yl)acetamide (57) as (peak 2, tR 7.20 min.); 1H NMR (500 MHz, METHANOL-d4) δ: 7.42-7.49 (m, 1H), 7.39 (br d, J=3.8 Hz, 1H), 6.99 (br d, J=4.5 Hz, 1H), 6.90-6.96 (m, 1H), 6.80 (br s, 1H), 6.66-6.77 (m, 1H), 1.99 (br s, 3H).

| Molecular Formula | Isotopic Mass | calculated mass for $MH^+$ | measured mass for $MH^+$ | LCMS [M + H]+ | UV RT (min) |
|---|---|---|---|---|---|
| $C_{17}H_{13}ClN_2O_4$ | 344.0564 | 345.0637 | 345.0638 | 345.1 | 2.02 |

and N-((4bS,9bS)-1-amino-7-chloro-4b-hydroxy-10-oxo-4b,10-dihydro-9bH-indeno[1,2-b]benzofuran-9b-yl)acetamide (58) as (peak 1, tR 4.92 min.); $^1H$ NMR (500 MHz, METHANOL-d4) δ: 7.47 (t, J=7.8 Hz, 1H), 7.41 (br d, J=8.3 Hz, 1H), 7.01 (d, J=7.3 Hz, 1H), 6.97 (br d, J=8.3 Hz, 1H), 6.82 (s, 1H), 6.76 (br s, 1H), 2.01 (s, 3H).

| Molecular Formula | Isotopic Mass | calculated mass for $MH^+$ | measured mass for $MH^+$ | LCMS [M + H]+ | UV RT (min) |
|---|---|---|---|---|---|
| $C_{17}H_{13}ClN_2O_4$ | 344.0564 | 345.0637 | 345.0634 | 345.1 | 2.02 |

Examples 16-18: N-(1-amino-4b-hydroxy-7-methyl-10-oxo-4b,10-dihydro-9bH-indeno[1,2-b]benzofuran-9b-yl)acetamide and N-((4bR,9bR)-1-amino-4b-hydroxy-7-methyl-10-oxo-4b,10-dihydro-9bH-indeno[1,2-b]benzofuran-9b-yl)acetamide and N-((4bS,9bS)-1-amino-4b-hydroxy-7-methyl-10-oxo-4b,10-dihydro-9bH-indeno[1,2-b]benzofuran-9b-yl)acetamide

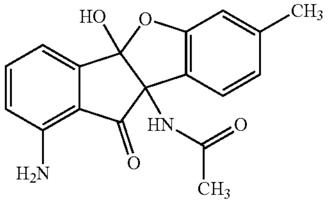

64

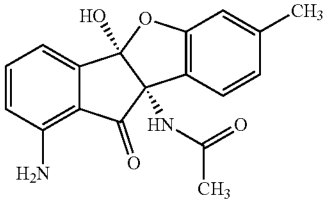

65

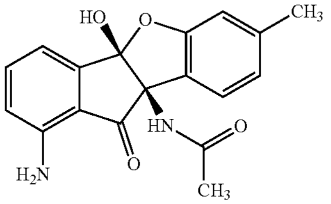

66

Scheme 8

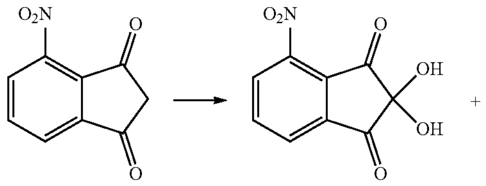

4 5

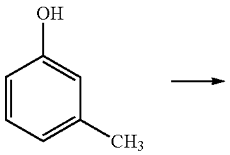

59

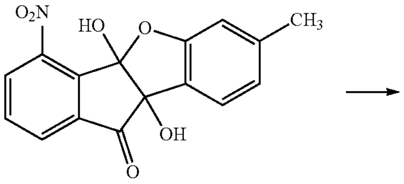

60

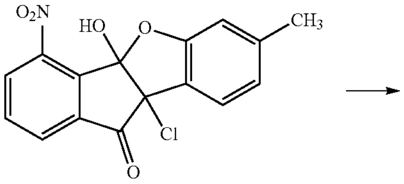

61

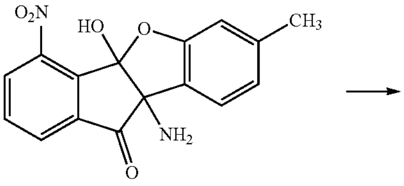

62

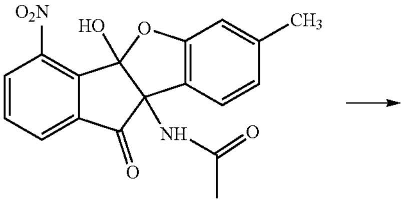

63

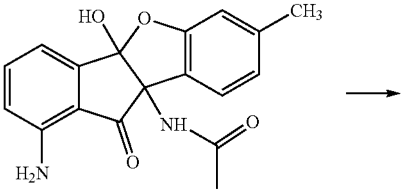

64

-continued

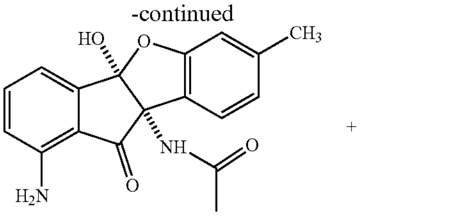

65

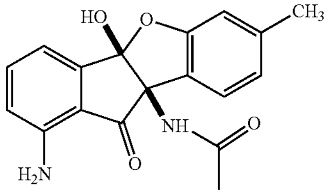

66

4b,9b-Dihydroxy-7-methyl-4-nitro-4b,9b-dihydro-10H-indeno[1,2-b]benzofuran-10-one (60)

2,2-dihydroxy-4-nitro-1H-indene-1,3(2H)-dione 5 (6.3 g, crude, 26.15 mmol) was suspended in gl. AcOH (44 mL). m-cresol 59 (3.0 mL, 28.77 mmol) was added. This resulting solution was refluxed at 120° C. for next 6 hours and then concentrated. This residue was purified over column chromatography (50% EA in hexane with 50% dichloromethane) and precipitated again to obtain pure product. $^1$H NMR (300 MHz, $CDCl_3$) δ 8.51 (dd, J=8.0, 0.8 Hz, 1H), 8.19 (dd, J=7.7, 0.9 Hz, 1H), 7.80 (t, J=7.8 Hz, 1H), 7.45 (d, J=7.8 Hz, 1H), 6.85 (d, J=7.8 Hz, 48H), 6.67 (s, 1H), 2.31 (s, 3H).

9b-Chloro-4b-hydroxy-7-methyl-4-nitro-4b,9b-dihydro-10H-indeno[1,2-b]benzofuran-10-one (61)

4b,9b-dihydroxy-7-methyl-4-nitro-4b,9b-dihydro-10H-indeno[1,2-b]benzofuran-10-one 60 (5.3 g, 16.91 mmol) was suspended in DCM (67 mL). Oxalyl chloride (1.7 mL, 20.3 mmol) was added slowly (5 min.) at ambient temperature and then dried DMF (5 mL) was added slowly at ambient temperature. This reaction mixture was stirred overnight at ambient temperature and diluted with DCM and washed with water. The organic layer was dried over anhydrous $Na_2SO_4$ and concentrated and then purified with column chromatography (25% EA in Hex with 25% DCM) and re-precipitated (DCM/Hex=½) to obtain the product. $^1$H NMR (300 MHz, $CDCl_3$) δ 8.53 (dd, J=8.0, 0.9 Hz, 1H), 8.23 (dd, J=7.7, 1.0 Hz, 1H), 7.83 (t, J=7.9 Hz, 1H), 7.44 (d, J=7.9 Hz, 1H), 6.89 (d, J=7.9 Hz, 1H), 6.68 (d, J=7.2 Hz, 1H), 6.34 (s, 1H), 2.32 (d, J=6.1 Hz, 3H).

9b-Amino-4b-hydroxy-7-methyl-4-nitro-4b,9b-dihydro-10H-indeno[1,2-b]benzofuran-10-one (62)

9b-chloro-4b-hydroxy-7-methyl-4-nitro-4b,9b-dihydro-10H-indeno[1,2-b]benzofuran-10-one 61 (2.29 g, 6.9 mmol.) was dissolved in dried THF (69 mL) then 2.0 M solution of $NH_3$ in IPA (6.9 mL) was added at −40° C. The reaction mixture was warmed to −10° C. and then stirred 3 hours, this reaction mixture was diluted with EA and washed with water. This organic layer was dried over anhydrous $Na_2SO_4$ and concentrated and then purified with column chromatography (33% EA in Hex with 3.3% DCM) and re-precipitated (DCM/Hex=½) then obtained a product. $^1$H NMR (300 MHz, $CDCl_3$) δ 8.52 (d, J=8.0 Hz, 1H), 8.14 (d, J=7.6 Hz, 1H), 7.75 (t, J=7.8 Hz, 1H), 7.31 (m, 1H), 6.83 (t, J=8.6 Hz, 1H), 6.67 (s, 1H), 2.30 (d, J=6.0 Hz, 3H).

N-(4b-Hydroxy-7-methyl-4-nitro-10-oxo-4b,10-dihydro-9bH-indeno[1,2-b]benzofuran-9b-yl)acetamide (63)

9b-amino-4b-hydroxy-7-methyl-4-nitro-4b,9b-dihydro-10H-indeno[1,2-b]benzofuran-10-one (310 mg, 1.0 mmol.) and acetic anhydride (0.113 mL, 1.2 mmol.) was dissolved acetic acid (10 mL). This resulting solution was stirred 2 hour at 80° C. This reaction mixture was cooled down room temperature and then diluted with EA and washed with water. The organic layer was dried over anhydrous $MgSO_4$ and concentrated and then purified with column chromatography (50% EA in Hexane with 5% DCM) and re-precipitated (DCM/Hex=½) to obtain the product. $^1$H NMR (300 MHz, $CDCl_3$) δ 8.47 (dd, J=8.1, 0.8 Hz, 1H), 8.22 (d, J=6.9 Hz, 1H), 7.76 (t, J=7.8 Hz, 1H), 7.42 (d, J=7.8 Hz, 1H), 6.85 (d, J=7.9 Hz, 1H), 6.64 (s, 1H), 6.50 (s, 1H), 6.08 (s, 1H), 2.31 (s, 3H), 2.10 (s, 3H).

N-(1-Amino-4b-hydroxy-7-methyl-10-oxo-4b,10-dihydro-9bH-indeno[1,2-b]benzofuran-9b-yl)acetamide (64)

N-(4b-hydroxy-7-methyl-4-nitro-10-oxo-4b,10-dihydro-9bH-indeno[1,2-b]benzofuran-9b-yl)acetamide 63 (150 mg, 0.4233 mmol.) was dissolved ethanol (8 mL). To this solution were added Iron powder (70 mg 1.27 mmol.), water (0.8 mL) and Conc-HCl (2-drops). This resulting solution was stirred 2 hour at 90° C. The reaction mixture was cooled down room temperature and filtered through CELITE pad. The filtrate was concentrated and then purified with column chromatography (50%-150% EA in Hex with 5% DCM) and re-precipitated with EA then obtain the product. $^1$H NMR (300 MHz, $CDCl_3$) δ 8.83 (s, 0.5H), 7.52 (m, 1.5H), 7.23 (m, 1.6H), 7.17 (d, J=7.5 Hz, 0.7H), 6.85 (m, 1H), 6.77 (d, J=7.8 Hz, 0.7H), 6.66 (m, 1.5H), 6.60 (d, J=8.1 Hz, 0.7H), 6.54 (brs, 0.3H), 5.76 (d, J=8.9 Hz, 1H), 5.55 (brs, 1H), 2.29 (s, 2H), 2.26 (s, 1H), 2.06 (s, 3H).

| Molecular Formula | Isotopic Mass | calculated mass for $MH^+$ | measured mass for $MH^+$ | LCMS [M + H]+ | UV RT (min) |
|---|---|---|---|---|---|
| $C_{18}H_{16}N_2O_4$ | 324.111 | 325.1183 | 325.1183 | 325.1 | 1.81 |

N-((4bR,9bR)-1-Amino-4b-hydroxy-7-methyl-10-oxo-4b,10-dihydro-9bH-indeno[1,2-b]benzofuran-9b-yl)acetamide (65) and N-((4bS,9bS)-1-Amino-4b-hydroxy-7-methyl-10-oxo-4b,10-dihydro-9bH-indeno[1,2-b]benzofuran-9b-yl)acetamide (66)

N-(1-Amino-4b-hydroxy-7-methyl-10-oxo-4b,10-dihydro-9bH-indeno[1,2-b]benzofuran-9b-yl)acetamide (64) (200 mg) was purified by chiral chromatography using (AD column, HPLC=20 ml/min, Heptane/IPA=70/30, 759 psi) to give N-((4bR,9bR)-1-Amino-4b-hydroxy-7-methyl-10-oxo-4b,10-dihydro-9bH-indeno[1,2-b]benzofuran-9b-yl)acetamide (65) as (peak 2, tR 12.49 min.); 1H NMR (500 mHz, METHANOL-d4) δ: 7.38-7.47 (m, 1H), 7.28-7.37 (m, 1H), 6.97 (br d, J=6.6 Hz, 1H), 6.79 (br d, J=6.9 Hz, 1H), 6.66 (br d, J=7.3 Hz, 1H), 6.59 (br s, 1H), 2.27 (s, 3H), 1.99 (s, 3H).

| Molecular Formula | Isotopic Mass | calculated mass for $MH^+$ | measured mass for $MH^+$ | LCMS [M + H]+ | UV RT (min) |
|---|---|---|---|---|---|
| $C_{18}H_{16}N_2O_4$ | 324.111 | 325.1183 | 325.1185 | 325.1 | 1.81 |

and N-((4bS,9bS)-1-Amino-4b-hydroxy-7-methyl-10-oxo-4b,10-dihydro-9bH-indeno[1,2-b]benzofuran-9b-yl)acetamide (66) as (peak 1, tR 7.77 min.); 1H NMR (500 MHz, METHANOL-d4) δ: 7.44 (br s, 1H), 7.34 (br s, 1H), 6.99 (br d, J=5.7 Hz, 1H), 6.80 (br d, J=6.1 Hz, 1H), 6.68 (br d, J=4.0 Hz, 1H), 6.61 (br s, 1H), 2.28 (s, 3H), 2.01 (s, 3H).

| Molecular Formula | Isotopic Mass | calculated mass for $MH^+$ | measured mass for $MH^+$ | LCMS [M + H]+ | UV RT (min) |
|---|---|---|---|---|---|
| $C_{18}H_{16}N_2O_4$ | 324.111 | 325.1183 | 325.1183 | 325.1 | 1.81 |

Example 19: N-(1-amino-4b-hydroxy-8-methyl-10-oxo-4b,10-dihydro-9bH-indeno[1,2-b]benzofuran-9b-yl)acetamide

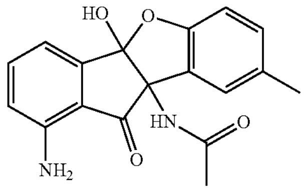 [SMILES: CC(=O)NC12C(=O)c3c(N)cccc3C1(O)Oc1ccc(C)cc12]

Procedure for the above compound follows a similar route as mentioned in Examples 16-18, except p-cresol was used instead of m-cresol to give the product N-(1-amino-4b-hydroxy-8-methyl-10-oxo-4b,10-dihydro-9bH-indeno[1,2-b]benzofuran-9b-yl)acetamide. $^1H$ NMR (500 MHz, METHANOL-d4) δ: 7.44 (br t, J=7.2 Hz, 1H), 7.30 (br s, 1H), 7.09 (br d, J=7.8 Hz, 1H), 6.99 (br d, J=6.9 Hz, 1H), 6.67 (br t, J=9.2 Hz, 2H), 2.30 (br s, 3H), 2.01 (s, 3H).

| Molecular Formula | Isotopic Mass | calculated mass for $MH^+$ | measured mass for $MH^+$ | LCMS [M + H]+ | UV RT (min) |
|---|---|---|---|---|---|
| $C_{18}H_{16}N_2O_4$ | 324.111 | 325.1183 | 325.1182 | 325.1 | 1.82 |

Example 20: N-((4bR,9bR)-1-amino-4b-hydroxy-8-methyl-10-oxo-4b,10-dihydro-9bH-indeno[1,2-b]benzofuran-9b-yl)acetamide

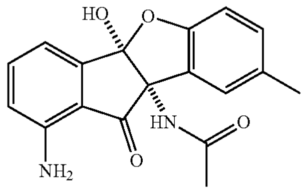 [SMILES: CC(=O)N[C@]12C(=O)c3c(N)cccc3[C@@]1(O)Oc1ccc(C)cc12]

The racemate N-(1-amino-4b-hydroxy-8-methyl-10-oxo-4b,10-dihydro-9bH-indeno[1,2-b]benzofuran-9b-yl)acetamide (200 mg) was purified by chiral chromatography using (AD column, SFC=100 ml/min, CO2/EtOH=75/25, 226 bar) to give the product above N-((4bR,9bR)-1-amino-4b-hydroxy-8-methyl-10-oxo-4b,10-dihydro-9bH-indeno[1,2-b]benzofuran-9b-yl)acetamide as (peak 2, tR 5.43 min.); 1H NMR (400 MHz, METHANOL-d4) δ: 7.42 (br t, J=7.1 Hz, 1H), 7.27 (br s, 1H), 7.06 (br d, J=7.9 Hz, 1H), 6.97 (br d, J=6.8 Hz, 1H), 6.64 (br d, J=8.1 Hz, 2H), 2.28 (s, 3H), 1.98 (s, 3H) and also N-((4bS,9bS)-1-amino-4b-hydroxy-8-methyl-10-oxo-9b,10-dihydro-4bH-indeno[1,2-b]benzofuran-9b-yl)acetamide as (peak 1, tR 3.68 min.).

| Molecular Formula | Isotopic Mass | calculated mass for $MH^+$ | measured mass for $MH^+$ | LCMS [M + H]+ | UV RT (min) |
|---|---|---|---|---|---|
| $C_{18}H_{16}N_2O_4$ | 324.111 | 325.1183 | 325.1184 | 325.1 | 1.82 |

Example 21: N-(1-amino-4b-hydroxy-10-oxo-7-(trifluoromethyl)-4b,10-dihydro-9bH-indeno[1,2-b]benzofuran-9b-yl)-N-methlacetamide

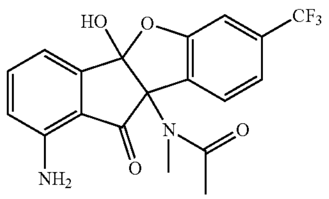 [SMILES: CC(=O)N(C)C12C(=O)c3c(N)cccc3C1(O)Oc1cc(C(F)(F)F)ccc12]

Procedure for the above compound followed a similar route as mentioned in Example 3-5, except 2.0 M methyl amine in THF was used instead of 2.0 M ammonia in IPA to give the product N-(1-amino-4b-hydroxy-10-oxo-7-(trifluoromethyl)-4b,10-dihydro-9bH-indeno[1,2-b]benzofuran-9b-yl)-N-methylacetamide. 1H NMR (500 MHz, METHANOL-d4) δ: 7.63 (br d, J=7.6 Hz, 1H), 7.44 (br t, J=7.8 Hz, 1H), 7.31 (br d, J=8.0 Hz, 1H), 7.10 (s, 1H), 6.99 (br d, J=7.3 Hz, 1H), 6.70 (br d, J=7.3 Hz, 1H), 2.88 (s, 3H), 2.19 (s, 3H).

| Molecular Formula | Isotopic Mass | calculated mass for $MH^+$ | measured mass for $MH^+$ | LCMS [M + H]+ | UV RT (min) |
|---|---|---|---|---|---|
| $C_{19}H_{15}F_3N_2O_4$ | 392.0984 | 393.1057 | 393.1055 | 393.1 | 2.31 |

Examples 22-24: N-(1-amino-4b-hydroxy-7-methoxy-10-oxo-4b,10-dihydro-9bH-indeno[1,2-b]benzofuran-9b-yl)acetamide (Example 22), N-((4bR,9bR)-1-amino-4b-hydroxy-7-methoxy-10-oxo-4b,10-dihydro-9bH-indeno[1,2-b]benzofuran-9b-yl)acetamide (Example 23), and N-((4bS,9bS)-1-amino-4b-hydroxy-7-methoxy-10-oxo-4b,10-dihydro-9bH-indeno[1,2-b]benzofuran-9b-yl)acetamide (Example 24)

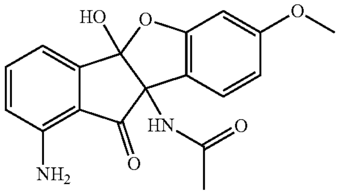

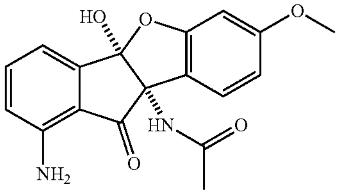

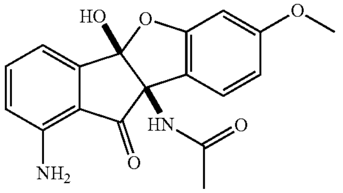

Procedure for the above compound followed a similar route as mentioned in Examples 16-18, except 3-methoxy phenol was used instead of m-cresol to give the racemate N-(1-amino-4b-hydroxy-7-methoxy-10-oxo-9b,10-dihydro-4bH-indeno[1,2-b]benzofuran-9b-yl)acetamide (Example 22) (200 mg) which was purified by chiral chromatography using (AD column, HPLC=20 ml/min, Heptane/IPA=70/30, 723 psi) to give the product above N-((4bR,9bR)-1-amino-4b-hydroxy-7-methoxy-10-oxo-4b,10-dihydro-9bH-indeno[1,2-b]benzofuran-9b-yl)acetamide as (peak 2, tR 24.20 min.); 1H NMR (500 MHz, METHANOL-d4) δ: 7.39-7.50 (m, 1H), 7.31 (br dd, J=3.1, 2.4 Hz, 1H), 6.92-7.05 (m, 1H), 6.62-6.74 (m, 1H), 6.44-6.57 (m, 1H), 6.34 (s, 1H), 3.72 (s, 3H), 1.99 (s, 3H) (Example 23) and also N-((4bS,9bS)-1-amino-4b-hydroxy-7-methoxy-10-oxo-9b,10-dihydro-4bH-indeno[1,2-b]benzofuran-9b-yl)acetamide as (peak 1, tR 9.78 min.) (Example 24).

| Molecular Formula | Isotopic Mass | calculated mass for $MH^+$ | measured mass for $MH^+$ | LCMS [M + H]+ | UV RT (min) |
|---|---|---|---|---|---|
| $C_{18}H_{16}N_2O_5$ | 340.1059 | 341.1132 | 341.1132 | 341.1 | 1.63 |

Bioactivity of the compounds of the invention was determined using the following methods.

Determination of Drug Efficacy Against Picornaviruses Using Cytopathic Effect (CPE) Inhibition Assay In the assay, HeLa (human cervical cancer cells), MRC-5 (human fetal lung fibroblast cells), and RD cells (derived from human rhabdomyosarcoma) were employed. For comparison, ribavirin (Riv), Pleconaril (pleco), and BTA-798 (BTA) were used as controls. Reagents were dissolved at a concentration of 10-40 mg/ml in 100% dimethyl sulfoxide (DMSO). Water-soluble reagents were dissolved in PBS (−) solution and stored at −20° C. On the day of the experiment, they were used in 3 fold to 5 fold concentrations in such a manner that the concentration of dimethyl sulfoxide in each well was between 0.5% and 1%.

Pharmaceutical efficacy was determined using a virus-induced cytopathic effect (CPE) inhibition assay. In this regard, after cells suitable for viruses were grown in 96-well plates, dilutions of viruses in DME supplemented with 2% FBS (DME/2% FBS) or MEM supplemented with 2% FBS (MEM/2% FBS) were inoculated in an amount of 100 μl with a concentration corresponding to 100 $CCID_{50}$ (50% cell culture infective dose) into each well of the plates, and incubated for 30 min-1 hr at 33° C. or 37° C. to allow the viruses to adsorb onto the cells. The culture medium was removed before aliquots of drug dilutions with various concentrations were added in an amount of 100 μl to each well. While HRV (human rhinovirus) was grown at 33° C., the other viruses were incubated in a 37° C. CO2 incubator for 2-3 days. Alternatively, the cells were cultured for 2-3 days without removal of the medium after they were added with 50 μl of each drug dilution having a 2-fold higher concentration and then with 50 μl of the virus dilution. Viruses were incubated in host HeLa cells at 37° C. for 2-3 days in DME/2% or MEM/2% FBS.

For HeLa cells, the drugs were measured for $EC_{50}$ (50% maximal effective concentration), which is the concentration of a drug inducing a response halfway between the baseline and maximum, using an MTT assay. With regard to RD and MRC-5 cells, CPE was determined using FDA (Fluorescein diacetate) or MTT. In order to determine the effect of drug toxicity on efficacy results, at the time of inoculation with the virus, mock-infection was also included. A virus-free medium was added to a cell culture, which was then subjected to the same treatment as the virus-infected cells inoculated with the virus. That is, the medium was removed after one hour of incubation, and dilutions of drugs in the medium were added once more. Following incubation for 2-3 days, the cells were observed under a microscope and the drugs were determined for $CC_{50}$ (50% cytotoxic concentration) at which 50% of the cells were killed, using an MTT assay in which counts of viable cells in mock-infected wells containing drugs were compared to those of viable cells in control wells containing no drugs. In an FDA hydrolysis assay, FDA was added to each well after removal of the medium, and incubated for 20-30 min before fluorescence intensity was measured using a spectrofluorometer to determine CPE in the same manner as in MTT.

That is, the survival rate (% survival) of mock-infected cells for cytotoxicity measurement was calculated using the Mathematical Formula 1 below:

Cell Drug=Survival by [$A$ (Drug)−$A$ (Background solution)/$A$ (Cell control)−(Background×100% Solution)]

While 100% cell survival means no cytotoxicity of the drug, the highest cytotoxicity is reflected by 0% cell survival. The 50% cytotoxic concentration was defined as the concentration required to reduce the cell number by 50%. This concentration of the drug is represented as $CC_{50}$. Higher values mean lower cytotoxicity.

In addition, antiviral effects can be calculated using Mathematical Formula 2 below:

Antiviral Effect=[*A* (Drug/Virus)−*A* (Virus Control)/*A* (Cell control)−*A* (Virus Control)]

If the survival rate is 100%, its antiviral effect is 100% whereas if the survival rate is 0%, its antiviral effect is none. While the concentration of a drug at which the cell in a well infected with a virus can exhibit 50% survival rate is calculated as $EC_{50}$, the lower this value is, the more superior the antiviral effect is.

In Table 1 below are listed $CC_{50}$ concentrations that exhibit cytotoxicity against the compounds in some examples and $EC_{50}$ concentrations that exhibit activities against a number of rhinoviruses belonging to the picornaviruses.

Determination of Drug Effect Against Picornaviruses Using Multicycle Cytopathic Effect (CPE) Reduction Assay The multicycle CPE reduction assay was used to conduct determination of drug efficacy against picornaviruses. The antiviral activity of a compound was initially determined by the CPE reduction assay based on MIS [3-(4,5-dimethyl thiazol-2-yl)-5-(3-carboxy methoxy phenyl)-2-(4-sulfophenyl)-2H-tetrazolium.

Specifically, cells grown to confluence in 96-well plates were infected with 100 50% cell culture infected doses ($CCID_{50}$) of virus. After an adsorption period of 2 hrs at 37° C., the virus was removed and serial dilutions of the compounds were added. The cultures were further incubated at 37° C., for 3 days until complete CPE was observed in the infected and untreated virus control (VC). After removal of the medium, 90 μl of a culture medium and 10 μl of MTS-phenazine methosulfate (Promega, Leiden, The Netherlands) were added to each well. After an incubation period of 2 hrs at 37° C., the optical density (OD) of each well was read at 498 nm in a microplate reader.

The % CPE values for evaluating antiviral activity were calculated using Mathematical Formula 3 below:

% CPE=100×[OD (CC)−OD (Virus+Compound)/OD (CC)−OD (VC)]

The % CPE value for measuring cytotoxicity of a drug was calculated by Mathematical Formula 4 below:

% CPE=100×[OD (CC)−OD (Virus+Compound)/OD (CC)−OD (Blank)]

In Mathematical Formulae 3 and 4 above,

- OD (CC) represents the OD of the background cell culture that is neither induced by a virus nor treated by chemical,
- OD (VC) represents the OD of the control cell culture that is induced by a virus but not treated by chemical,
- OD (Virus+Compound) represents the OD of the cell culture infected by a virus that has been treated with a concentrated compound,
- OD (Compound) represents the OD of the cell culture that has been treated with a concentrated compound only, and OD (Blank) represents the OD of the well to which only the cell culture has been added.

The effective concentration ($EC_{50}$) represents the concentration of a drug at which 50% of cells are allowed to survive by CPE of an induced virus, and the cytotoxicity concentration ($CC_{50}$) represents the concentration of a drug at which a compound has killed 50% of cells, and they were calculated by the logarithmic interpolation.

In Table 1 below are listed the toxicity concentrations ($CC_{50}$) and effective concentrations ($EC_{50}$) against various viruses for some compounds of the examples.

TABLE 1

| Example No. | Cox B4 ($EC_{50}$ μM) | PV1 ($EC_{50}$ μM) | CYTOTOX ($EC_{50}$ μM) | A16_CPE ($EC_{50}$ μM) | HRV B14 CPE) ($EC_{50}$ μM) | C15_C3 REP (CC50 μM) |
|---|---|---|---|---|---|---|
| 1 | 0.00061 | 0.01500 | 50.000 | 1.891 | 0.016 | 35.075 |
| 3 | 0.00201 | | 50.000 | 50.000 | 0.019 | 21.407 |
| 4 | 0.00059 | 0.04100 | 50.000 | | | |
| 5 | 0.04422 | 9.22000 | 50.000 | | | 25 |
| 6 | 0.00098 | | 50.000 | 43.267 | 0.049 | 50.000 |
| 7 | 0.00168 | | 50.000 | 14.683 | 0.016 | 50.000 |
| 8 | 0.00093 | 0.02800 | 50.000 | 7.849 | 0.025 | 50.000 |
| 9 | 0.08615 | | 50.000 | 50.000 | 3.208 | 50.000 |
| 10 | 0.00303 | 0.33500 | 50.000 | 39.810 | 0.056 | 50.000 |
| 11 | 0.00110 | | 50.000 | | | |
| 12 | 0.18831 | 0.01500 | 50.000 | 1.891 | 0.016 | |
| 13 | 0.00267 | 0.29500 | 50.000 | | | |
| 14 | 0.00182 | | 50.000 | | | |
| 15 | 0.28951 | | 50.000 | | | 25 |
| 16 | 0.00374 | | 50.000 | 50.000 | 0.076 | |
| 17 | 0.00174 | 0.11000 | 50.000 | | | |
| 18 | 0.38336 | | 50.000 | | | 25 |
| 19 | 0.00871 | 3.23800 | 50.000 | 50.000 | 0.666 | 25 |
| 20 | 0.00443 | 2.17000 | 50.000 | | | |
| 21 | 0.00320 | | 50.000 | | | 25 |
| 23 | 0.00293 | | 50.000 | | | |

As is indicated in Table 1 above, most of the compounds according to the present invention exhibit high $CC_{50}$ concentrations so are found to have low cytotoxicity. In addition, the novel compounds according to the present invention were mostly found to have very high antiviral activities against a number of rhinoviruses (HRV). In addition, it was found that the novel compounds according to the present invention mostly had high antiviral activities against coxsackievirus B4 (Cox B4) and poliovirus 1 (PV1).

Therefore, since the compounds according to the present invention exhibit low cytotoxicity and high antiviral activities against various rhinoviruses, they may be usefully used for a pharmacological composition for preventing or treating diseases caused by the picornaviruses to which they belong.

Therefore, since the compounds according to the present invention have low cytotoxicity and exhibit superior antiviral activities against picornaviruses to which coxsackieviruses, polioviruses and rhinoviruses belong, they can be used effectively for prevention or treatment of the diseases caused by such viruses, for example, respiratory, cardiocirculatory, and nervous system diseases, including poliomyelitis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, flu, herpangina, foot-and-mouth disease, asthma, chronic obstructive pulmonary disease, pneumonia, sinusitis and otitis media.

As the compounds expressed in Formulae according to the present invention that are in equilibria with each other have not only low cytotoxicity but also very superior antiviral activities against picornaviruses including coxsackieviruses, enteroviruses, echoviruses, polioviruses and rhinoviruses, they can be used effectively as pharmaceutical compositions for prevention or treatment of viral disease such as poliomyelitis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, flu, herpangina, foot-and-mouth disease, asthma, chronic obstructive pulmonary disease, pneumonia, sinusitis or otitis media.

The invention claimed is:

1. A compound of Formula [I], or a pharmaceutically acceptable salt thereof:

[I]

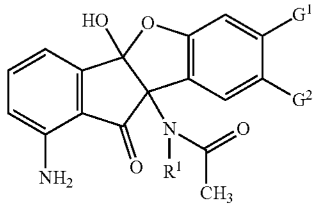

wherein, one of $G^1$ and $G^2$ is selected from linear or branched $C_1$-$C_5$ alkyloxy; linear or branched $C_1$-$C_5$ haloalkyl; linear or branched $C_1$-$C_5$ haloalkyloxy; halo and 3-7 membered cycloalkyl; and the other of $G^1$ and $G^2$ is H; and $R^1$ is selected from H and linear or branched $C_1$-$C_5$ alkyl.

2. The compound of claim 1, or the pharmaceutically acceptable salt thereof, wherein $G^1$ is selected from linear or branched $C_1$-$C_5$ haloalkyl; linear or branched $C_1$-$C_5$ haloalkyloxy; and 3-7 membered cycloalkyl.

3. The compound of claim 1, or the pharmaceutically acceptable salt thereof, wherein $G^1$ is linear or branched $C_1$-$C_5$ haloalkyl.

4. The compound of claim 1, or the pharmaceutically acceptable salt thereof, wherein $G^1$ is $CF_3$.

5. The compound of claim 1, or the pharmaceutically acceptable salt thereof, wherein $G^1$ is linear or branched $C_1$-$C_5$ haloalkyloxy.

6. The compound of claim 1, or the pharmaceutically acceptable salt thereof, wherein $G^1$ is $OCF_3$.

7. The compound of claim 1, or the pharmaceutically acceptable salt thereof, wherein $G^1$ is 3-7 membered cycloalkyl.

8. The compound of claim 1, or the pharmaceutically acceptable salt thereof, wherein $G^1$ is cyclopropyl.

9. The compound of claim 1, or the pharmaceutically acceptable salt thereof, wherein $G^2$ is H.

10. The compound of claim 1, or the pharmaceutically acceptable salt thereof, wherein $G^1$ is $OCH_3$.

11. The compound of claim 1, or the pharmaceutically acceptable salt thereof, wherein $G^1$ is halo.

12. The compound of claim 1, or the pharmaceutically acceptable salt thereof, wherein $G^1$ is H.

13. The compound of claim 1, or a pharmaceutically acceptable salt thereof, wherein the compound is of Formula [II]:

[II]

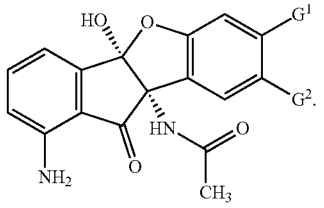

14. The compound of claim 1, or a pharmaceutically acceptable salt thereof, having Formula [III]:

[III]

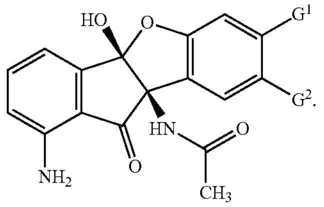

15. The compound of claim 1, or a pharmaceutically acceptable salt thereof, wherein the compound is of Formula [IV]:

[IV]

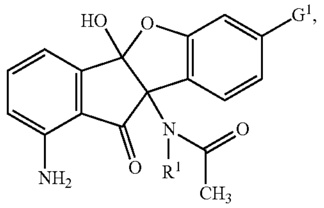

wherein $G^1$ is selected from linear or branched $C_1$-$C_5$ haloalkyl; linear or branched $C_1$-$C_5$ haloalkyloxy; and 3-7 membered cycloalkyl.

16. The compound of claim 15, wherein $G^1$ is selected from $CF_3$, $OCF_3$, and cyclopropyl.

17. The compound of claim 1, wherein $R^1$ is selected from H and methyl.

18. A compound, selected from:
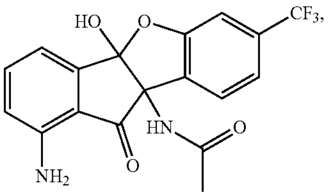
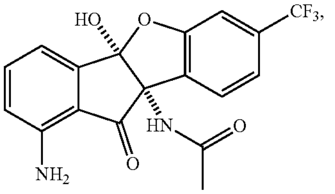
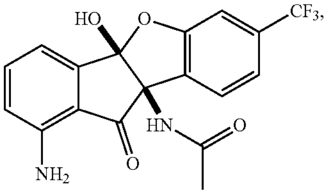
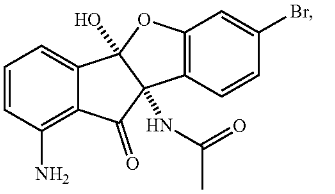
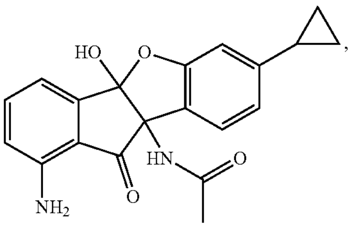
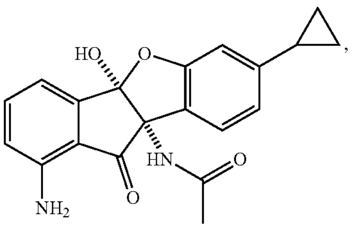
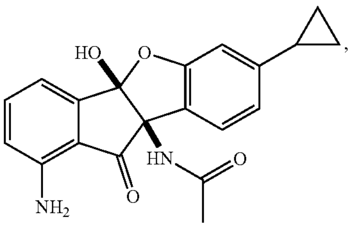
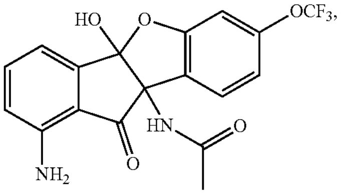
-continued
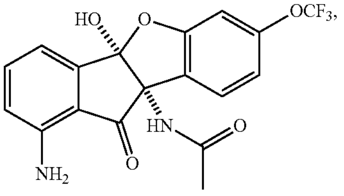
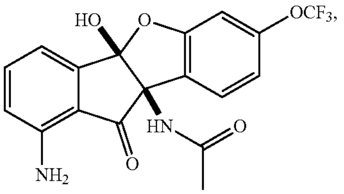
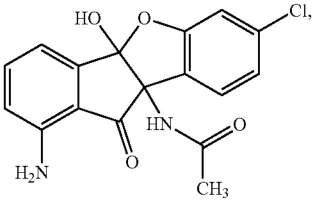
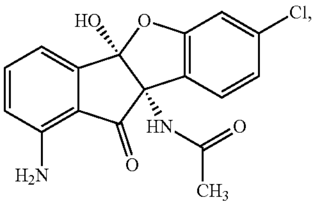
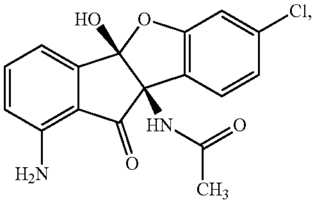
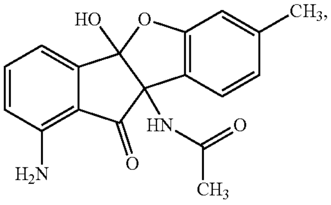
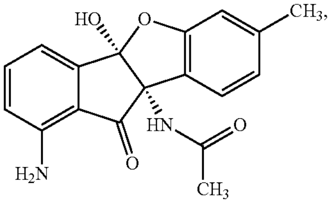
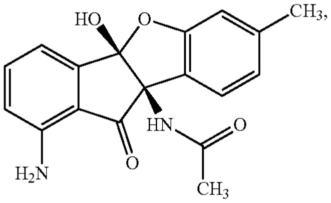

-continued

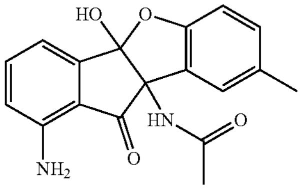

,

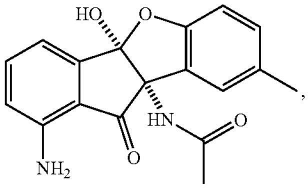

,

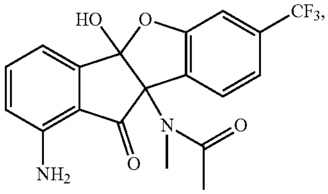

and

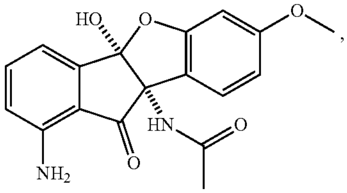

, or a pharmaceutically acceptable salt thereof.

19. A pharmaceutical composition comprising the compound of claim 1, a pharmaceutically acceptable salt thereof or optical isomer thereof and a pharmaceutically acceptable diluent or excipient.

20. A method of ameliorating or modulating a viral disease comprising administering to a subject in need thereof a therapeutically effective amount of a compound according to claim 1 or a pharmaceutically acceptable salt thereof.

21. The method of claim 20, wherein the viral disease is caused by one of coxsackievirus, poliovirus, echovirus, enterovirus, rhinovirus, and picornavirus.

22. The method of claim 20, wherein the viral disease is poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, flu, herpangina, foot-and-mouth disease, asthma, chronic obstructive pulmonary disease, pneumonia, sinusitis or otitis media.

23. The compound of claim 1, which is

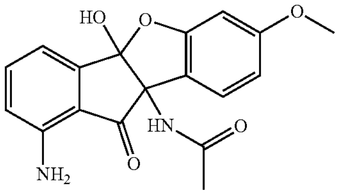

or

-continued

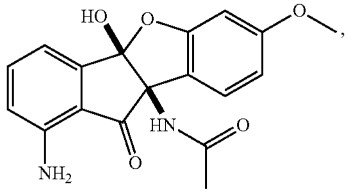

, or a pharmaceutically acceptable salt thereof.

24. A pharmaceutical composition the compound of claim 23, a pharmaceutically acceptable salt thereof or optical isomer thereof and a pharmaceutically acceptable diluent or excipient.

25. A method of ameliorating or modulating a viral disease comprising administering to a subject in need thereof a therapeutically effective amount of a compound of claim 23 or a pharmaceutically acceptable salt thereof.

26. The method of claim 25, wherein the viral disease is caused by one of coxsackievirus, poliovirus, echovirus, enterovirus, rhinovirus, and picornavirus.

27. The method of claim 25, wherein the viral disease is poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, flu, herpangina, foot-and-mouth disease, asthma, chronic obstructive pulmonary disease, pneumonia, sinusitis or otitis media.

28. The compound of claim 1, having the structure:

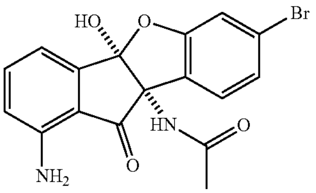 [SMILES: CC(=O)N[C@]12C(=O)c3c(N)cccc3[C@@]1(O)Oc1cc(Br)ccc12]

or a pharmaceutically acceptable salt thereof.

29. The compound of claim 1, having the structure:

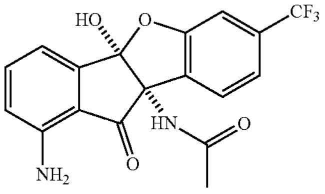 [SMILES: CC(=O)N[C@]12C(=O)c3c(N)cccc3[C@@]1(O)Oc1cc(C(F)(F)F)ccc12]

or a pharmaceutically acceptable salt thereof.

30. The compound of claim 1, having the structure:

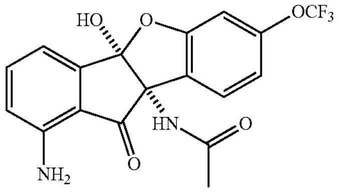 [SMILES: CC(=O)N[C@]12C(=O)c3c(N)cccc3[C@@]1(O)Oc1cc(OC(F)(F)F)ccc12]

or a pharmaceutically acceptable salt thereof.

31. The compound of claim 1, having the structure:
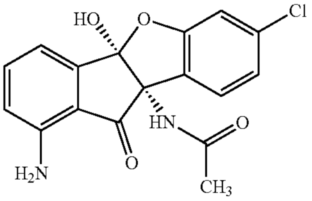 [SMILES: CC(=O)N[C@]12C(=O)c3c(N)cccc3[C@@]1(O)Oc1cc(Cl)ccc12]
or a pharmaceutically acceptable salt thereof.
* * * * *